US010717996B2

(12) United States Patent
Dusseaux et al.

(10) Patent No.: US 10,717,996 B2
(45) Date of Patent: Jul. 21, 2020

(54) RECOMBINANT YEAST CELLS PRODUCING POLYLACTIC ACID AND USES THEREOF

(71) Applicants: CARBIOS, Saint-Beauzire (FR); INSTITUT NATIONAL DE LA RECHERCHE AGRONOMIQUE, Paris (FR); INSTITUT NATIONAL DES SCIENCES APPLIQUEES, Toulouse (FR); CENTRE NATIONAL DE LA RECHERCHE SCIENTIFIQUE, Paris (FR)

(72) Inventors: Simon Dusseaux, Reims (FR); Sophie Lajus, Ayguesvives (FR); Vinciane Borsenberger, Toulouse (FR); Jonathan Verbeke, Toulouse (FR); Florence Bordes, Toulouse (FR); Alain Marty, Toulouse (FR); Jean-Marc Nicaud, Trappes (FR); Athanasios Beopoulos, Paris (FR)

(73) Assignees: CARBIOS, Saint-Beauzire (FR); INSTITUT NATIONAL DE RECHERCHE POUR L'AGRICULTURE, A'ALIMENTATION ET L'ENVIRONNEMENT, Paris (FR); INSTITUT NATIONAL DES SCIENCES APPLIQUEES, Toulouse (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 16/064,494

(22) PCT Filed: Dec. 15, 2016

(86) PCT No.: PCT/EP2016/081205
§ 371 (c)(1),
(2) Date: Jun. 21, 2018

(87) PCT Pub. No.: WO2017/108577
PCT Pub. Date: Jun. 29, 2017

(65) Prior Publication Data
US 2019/0002933 A1 Jan. 3, 2019

(30) Foreign Application Priority Data

Dec. 21, 2015 (EP) ..................... 15307084

(51) Int. Cl.
| | |
|---|---|
| *C12P 7/56* | (2006.01) |
| *C12N 1/16* | (2006.01) |
| *C08G 63/08* | (2006.01) |
| *C12P 7/62* | (2006.01) |
| *C12N 15/81* | (2006.01) |
| *C12N 9/10* | (2006.01) |

(52) U.S. Cl.
CPC ............... *C12P 7/56* (2013.01); *C08G 63/08* (2013.01); *C12N 1/16* (2013.01); *C12N 9/1029* (2013.01); *C12N 9/13* (2013.01); *C12N 15/815* (2013.01); *C12P 7/625* (2013.01); *C12Y 208/03001* (2013.01)

(58) Field of Classification Search
CPC ........ C08G 63/08; C12N 1/16; C12N 9/1029; C12N 9/13; C12N 15/815; C12P 7/56; C12P 7/625; C12Y 208/03001
See application file for complete search history.

(56) References Cited

U.S. PATENT DOCUMENTS

| | | | |
|---|---|---|---|
| 5,032,512 | A | 7/1991 | Witholt et al. |
| 5,145,779 | A | 9/1992 | Pometto, et al. |
| 5,212,219 | A | 5/1993 | Griffin |
| 5,316,847 | A | 5/1994 | Suominen |
| 5,378,738 | A | 1/1995 | Deguchi et al. |
| 5,426,047 | A | 6/1995 | Ito et al. |
| 6,312,578 | B1 | 11/2001 | Canivenc et al. |
| 6,429,006 | B1 | 8/2002 | Porro et al. |
| 7,465,575 | B2 | 12/2008 | Nilsson |
| 7,534,597 | B2 | 5/2009 | Hause et al. |
| 7,960,154 | B1 | 6/2011 | Nakajima et al. |
| 8,137,953 | B2 | 3/2012 | Miller et al. |
| 8,476,056 | B2 | 7/2013 | Hoang et al. |
| 8,614,076 | B2 | 12/2013 | Wada et al. |

(Continued)

FOREIGN PATENT DOCUMENTS

| | | |
|---|---|---|
| CN | 101 457 218 | 6/2009 |
| CN | 102250379 | 11/2011 |

(Continued)

OTHER PUBLICATIONS

Broun et al., Catalytic plasticity of fatty acid modification enzymes underlying chemical diversity of plant lipids. Science, 1998, vol. 282: 1315-1317. (Year: 1998).*

(Continued)

*Primary Examiner* — Ganapathirama Raghu

(74) *Attorney, Agent, or Firm* — Saliwanchik, Lloyd & Eisenschenk

(57) ABSTRACT

The present invention relates to a recombinant yeast cell comprising a gene encoding a protein exhibiting lactyl-CoA synthase activity and a gene encoding a protein exhibiting lactyl-CoA polymerase activity, said recombinant cell having the ability of producing polylactic acid (PLA), and the uses thereof.

20 Claims, 8 Drawing Sheets

Figure 1:
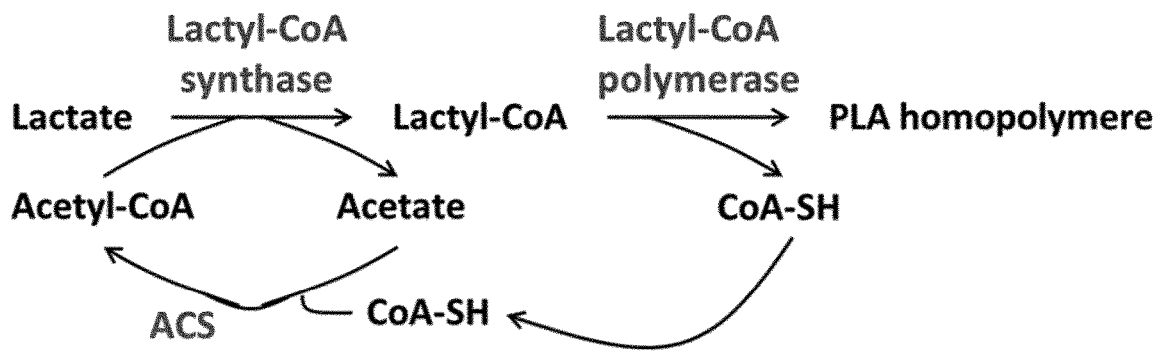

Specification includes a Sequence Listing.

(56) References Cited

U.S. PATENT DOCUMENTS

| | | | |
|---|---|---|---|
| 8,859,260 | B2 | 10/2014 | Sawai et al. |
| 9,217,165 | B2* | 12/2015 | Na .................. C12P 7/56 |
| 9,476,073 | B2 | 10/2016 | Boisart |
| 9,528,132 | B2 | 12/2016 | Mazzoli et al. |
| 10,124,512 | B2 | 11/2018 | Boisart et al. |
| 2005/0261465 | A1 | 11/2005 | Nagarajan |
| 2006/0106120 | A1 | 5/2006 | Abe et al. |
| 2011/0008855 | A1 | 1/2011 | Park et al. |
| 2011/0200771 | A1 | 8/2011 | Barclay |
| 2011/0245057 | A1 | 10/2011 | Scoledes et al. |
| 2011/0319588 | A1 | 12/2011 | Coupin et al. |
| 2012/0184005 | A1 | 7/2012 | Ferreira et al. |
| 2013/0274373 | A1 | 10/2013 | Yoshikawa et al. |
| 2014/0303278 | A1 | 10/2014 | Ferreira et al. |
| 2015/0056673 | A1 | 2/2015 | Boisart |
| 2015/0290840 | A1 | 10/2015 | Boisart et al. |
| 2016/0280881 | A1 | 9/2016 | Boisart et al. |
| 2017/0114205 | A1 | 4/2017 | Maille |
| 2017/0313998 | A1 | 11/2017 | Alvarez et al. |
| 2017/0349723 | A1 | 12/2017 | Ferreira et al. |
| 2018/0051264 | A1 | 2/2018 | Li et al. |
| 2018/0142097 | A1 | 5/2018 | Guemard et al. |
| 2018/0186943 | A1 | 7/2018 | Chateau et al. |

FOREIGN PATENT DOCUMENTS

| | | |
|---|---|---|
| CN | 102675712 | 9/2012 |
| CN | 103980535 | 8/2014 |
| EP | 0 421 413 | 4/1991 |
| EP | 0 738 752 | 10/1996 |
| EP | 1 548 053 | 6/2005 |
| EP | 2 013 280 | 1/2009 |
| EP | 2 348 122 | 7/2011 |
| EP | 2 377 945 | 10/2011 |
| EP | 2 471 910 | 7/2012 |
| EP | 2 626 386 | 8/2013 |
| JP | 2000-506442 | 5/2000 |
| JP | 2002-293982 | 10/2002 |
| JP | 2002-320499 | 11/2002 |
| JP | 2002 362578 | 12/2002 |
| JP | 2003-079388 | 3/2003 |
| JP | 2003-128835 | 5/2003 |
| JP | 2004 058010 | 2/2004 |
| JP | 2004-290130 | 10/2004 |
| JP | 2004 292705 | 10/2004 |
| JP | 2007 319092 | 12/2007 |
| JP | 2012 149273 | 8/2012 |
| JP | 2012-152171 | 8/2012 |
| JP | 2013 000099 | 1/2013 |
| JP | 5 630597 | 11/2014 |
| KR | 20110045975 | 5/2011 |
| WO | WO 89/10381 | 11/1989 |
| WO | WO 2005/026245 | 3/2005 |
| WO | WO 2010/012805 | 2/2010 |
| WO | WO 2010/081887 | 7/2010 |
| WO | WO 2011/039489 | 4/2011 |
| WO | WO 2013/144239 | 10/2013 |
| WO | WO 2014/079844 | 5/2014 |
| WO | WO 2014/122698 | 8/2014 |
| WO | WO 2014/167518 | 10/2014 |
| WO | WO 2014/167562 | 10/2014 |
| WO | WO 2015/067619 | 5/2015 |
| WO | WO 2015/097104 | 7/2015 |
| WO | WO 2015/173265 | 11/2015 |
| WO | WO 2016/198650 | 12/2016 |
| WO | WO 2016/198652 | 12/2016 |
| WO | WO 2017/198786 | 11/2017 |

OTHER PUBLICATIONS

Seffernick et al., Melamine deaminase and Atrazine chlorohydrolase: 98 percent identical but functionally different. J. Bacteriol., 2001, vol. 183 (8): 2405-2410. (Year: 2001).*

Written Opinion in International Application No. PCT/EP2017/062028, dated Jun. 30, 2017, pp. 1-5.
Matsuda, E. et al. "Gene Cloning and Molecular Characterization of an Extracellular Poly($_L$-Lactic Acid) Depolymerase from *Amycolatopsis* sp. Strain K104-1" *Journal of Bacteriology*, Nov. 2005, pp. 7333-7340, vol. 187, No. 21.
Database WPI, Accession No. 2009-K99963, Jun. 17, 2009, pp. 1-2, XP-002690934.
Database WPI, Accession No. 2008-F66138, Dec. 13, 2007, pp. 1-2, XP-002690935.
Wang, Z.-Y. et al. "Gene Cloning and Characterization of a Poly($_L$-Lactic Acid) Depolymerase from *Pseudomonas* sp. Strain DS04-T" *J Polym Environ*, Aug. 28, 2011, pp. 827-833, vol. 19, No. 4.
Akutsu-Shigeno, Y. et al. "Cloning and Sequencing of a Poly($_{DL}$-Lactic Acid) Depolymerase Gene from *Paenibacillus amylolyticus* Strain TB-13 and Its Functional Expression in *Escherichia coli*" *Applied and Environmental Microbiology*, May 2003, pp. 2498-2504, vol. 69, No. 5.
Petrov, K. et al. "$_L$(+)-Lactic acid production from starch by a novel amylolytic *Lactococcus lactis* subsp. lactis 884" *Food Microbiology*, Jun. 2008, pp. 550-557, vol. 25.
Currently pending claims of U.S. Appl. No. 14/443,524, 2016, pp. 1-4.
Bernard, N. et al. "Cloning of the D-lactate dehydrogenase gene from *Lactobacillus delbrueckii* subsp. bulgaricus by complementation in *Escherichia coli*" *FEBS*, Sep. 1991, pp. 61-64, No. 1.
Wieczorek, A. et al. "Engineering the cell surface display of cohesins for assembly of cellulosome-inspired enzyme complexes on *Lactococcus lactis*" *Microbial Cell Factories*, Sep. 2010, pp. 1-13, vol. 9, No. 69.
Wieczorek, A. et al. "Effects of synthetic cohesin-containing scaffold protein architecture on binding dockerin-enzyme fusions on the surface of *Lactococcus lactis*" *Microbial Cell Factories*, 2012, pp. 1-13, vol. 160, No. 11.
Koukiekolo, R. et al. "Degradation of Corn Fiber by *Clostridium cellulovorans* Cellulases and Hemicellulases and Contribution of Scaffolding Protein CbpA" Applied and Environmental Microbiology, Jul. 1, 2005, pp. 3504-3511, vol. 71, No. 7.
Cha, J. et al. "Effect of Multiple Copies of Cohesins on Cellulase and Hemicellulase Activities of *Clostridium cellulovorans* Minicellulosomes" *Journal of Microbiology and Biotechnology*, 2007, pp. 1782-1788, vol. 17, No. 11.
Kataeva, I. et al. "Interaction between *Clostridium thermocellum* endoglucanase CelD and polypeptides derived from the cellulosome-integrating protein CipA: stoichiometry and cellulolytic activity of the complexes" *Biochemical Journal*, 1997, pp. 617-624, vol. 326, No. 2.
Wen, F. et al. "Yeast Surface Display of Trifunctional Minicellulosomes for Simultaneous Saccharification and Fermentation of Cellulose to Ethanol" Applied and Environmental Microbiology, Feb. 1, 2010, pp. 1251-1260, vol. 76, No. 4.
Hyeon, J. E. et al. "Production of minicellulosomes for the enhanced hydrolysis of cellulosic substrates by recombinant *Corynebacterium glutamicum*" *Enzyme and Microbial Technology*, 2011, pp. 371-377, vol. 48.
Sun, J. et al. "Direct Conversion of Xylan to Ethanol by Recombinant *Saccharomyces cerevisiae* Strains Displaying an Engineered Minihemicellulosome" Applied and Environmental Microbiology, Jun. 2012, pp. 3837-3845, vol. 78, No. 11.
Database EMBL [Online] Accession No. HC441374, "Sequence 9 from Patent WO2010012805" Feb. 20, 2010, pp. 1-3, XP-002697306.
Database Geneseq [Online] Accession No. AZM34659, "Clostridium sp. Cellulose-binding protein-A (CbpA) DNA Seq: 6" Oct. 13, 2011, p. 1, XP-002697307.
Written Opinion in International Application No. PCT/EP2013/061413, dated Aug. 5, 2013, pp. 1-7.
Devos, D. et al. "Practical Limits of Function Prediction" *Proteins: Structure, Function and Genetics*, 2000, pp. 98-107, vol. 41.
Whisstock, J. C. et al. "Prediction of protein function from protein sequence and structure" *Quarterly Reviews of Biophysics*, 2003, pp. 307-340, vol. 36, No. 3.

(56) References Cited

OTHER PUBLICATIONS

Witkowski, A. et al. "Conversion of a β-Ketoacyl Synthase to a Malonyl Decarboxylase by Replacement of the Active-Site Cysteine with Glutamine" *Biochemistry*, 1999, pp. 11643-11650, vol. 38.
Kisselev, L. "Polypeptide Release Factors in Prokaryotes and Eukaryotes: Same Function, Different Structure" *Structure*, Jan. 2002, pp. 8-9, vol. 10.
Database WPI, Accession No. 2005-262580, Mar. 24, 2005, pp. 1-3, XP-002690554.
Database WPI, Accession No. 2004-751104, Oct. 21, 2004, pp. 1-2, XP-002690555.
Currently pending claims of U.S. Appl. No. 14/387,285, 2014, pp. 1-3.
Yoshida, S. et al. "A bacterium that degrades and assimilates poly(ethylene terephthalate)" *Science*, Mar. 11, 2016, pp. 1196-1199, vol. 351.
Demirel, B. et al. "Crystallization Behavior of PET Materials" *BAU Fen Bil. Enst. Dergisi Cilt*, 2011, pp. 26-35, vol. 13, No. 1.
Kyrikou, I. et al. "Biodegradation of Agricultural Plastic Films: A Critical review" *J Polym Environ*, 2007, pp. 125-150, vol. 15.
Chen, S. et al. "Identification and Characterization of Bacterial Cutinase" i*The Journal of Biological Chemistry*, Sep. 19, 2008, pp. 25854-25862, vol. 238, No. 38.
Ronkvist, A. M. et al. "Cutinase-Catalyzed Hydrolysis of Poly(ethylene terephthalate)" *Macromolecules*, 2009, pp. 5128-5138, vol. 42.
Nabil, H. et al. "Recycled Polyethylene Terephthalate Filled Natural Rubber Compounds: Effects of Filler Loading and Types of Matrix" *Journal of Elastomers and Plastics*, 2011, pp. 1-21, vol. 00-2011.
Bartolome, L. et al. "Recent Developments in the Chemical Recycling of PET" Material Recycling—Trends and Perspectives, Mar. 16, 2012, pp. 1-21.
Arutchelvi, J. et al. "Biodegradation of polyethylene and polypropylene" *Indian Journal of Biotechnology*, Jan. 2008, pp. 9-22, vol. 7.
Iwamoto, A. et al. "Enzymatic degradation of plastics containing polycaprolactone" *Polymer Degradation and Stability*, Jan. 1, 1994, pp. 205-213, vol. 45.
Mueller, R.-J. "Biological degradation of synthetic polyesters—Enzymes as potential catalysts for polyester recycling" *Process Biochemistry*, 2006, pp. 2124-2128, vol. 41, No. 10.
Written Opinion in International Application No. PCT/EP2014/073742, dated Aug. 8, 2015, pp. 1-5.
Herrero Acero, E. etal. "Enzymatic Surface Hydrolysis of PET: Effect of Structural Diversity on Kinetic Properties of Cutinases from *Thermobifida*" *Macromolecules*, 2011, pp. 4632-4640, vol. 44, No. 12.
Herrero Acero, E. et al. "Surface Engineering of a Cutinase From *Thermobifida Cellulosilytica* for Improved Polyester Hydrolysis" *Biotechnology & Bioengineering*, Oct. 2013, pp. 2581-2590, vol. 110, No. 10.
Shah, A. A. et al. "Degradation of aliphatic and aliphatic-aromatic co-polyesters by depolymerases from *Roseateles depolymerans* strain TB-87 and analysis of degradation products by LC-MS" *Polymer Degradation and Stability*, Oct. 16, 2013, pp. 2722-2729, vol. 98, No. 12.
Written Opinion in International Application No. PCT/EP2015/060521, dated Jul. 20, 2015, pp. 1-6.

Wikipedia, https://web.archive.org/web/20130424032652/https://en.wikipedia.org/wiki/Polyethylene_terephthalate, archived Apr. 24, 2013, accessed Aug. 13, 2018, pp. 1-13.
Sukkhum, S. et al. "A novel poly ($_L$-lactide) degrading actinomycetes isolated from Thai forest soil, phylogenic relationship and the enzyme characterization" *The Journal of General and Applied Microbiology*, 2009, pp. 459-467, vol. 55, No. 6.
Sukkhum, S. et al. "Poly($_L$-Lactide)-Degrading Enzyme Production by *Actinomadura keratinilytica* T16-1 in 3 L Airlift Bioreactor and Its Degradation Ability for Biological Recycle" *Journal of Microbiology and Biotechnology*, Jan. 28, 2012, pp. 92-99, vol. 22, No. 1.
Written Opinion in International Application No. PCT/EP2015/074222, dated Feb. 1, 2016, pp. 1-5.
Niaounakis, 2013. Chapter 4: Disposal. Biopolymers Reuse, Recycling, and Disposal. A Volume In Plastics Design Library, a PDL Handbook Series. ISBN 978-1-4557-3145-9, published by Elsevier Inc, pp. 107-150.
Sugimori, Mar. 2013. Protease, washing agent containing the protease, and method of manufacturing the washing agent. EMBL AB809463, pp. 1-2.
Albertsson, A- C. et al. "Chemistry and biochemistry of polymer biodegradation" *Chemistry and Technology of Biodegradable Polymers*, Jan. 1, 1994, pp. 7-17, Section 2.
Database WPI [Online] Accession No. 2012-Q50933, Sep. 9, 2012, p. 1, XP-002740253.
Database WPI [Online] Accession No. 2004-046313, May 8, 2003, pp. 1-2, XP-002740254.
Written Opinion in International Application No. PCT/EP2015/080557, dated Feb. 3, 2016, pp. 1-6.
Gouda, M. K. et al. "Production of a Polyester Degrading Extracellular Hydrolase from *Thermomonospora fusca*" *Biotechnology Progress*, Sep. 2002, pp. 927-934, vol. 18, No. 5.
Oda, Y. et al. "Degradation of Polylactide by Commercial Proteases" *Journal of Polymers and the Environment*, Jan. 2000, pp. 29-32, vol. 8, No. 1.
Written Opinion in International Application No. PCT/EP2016/055348, dated Jun. 2, 2016, pp. 1-6.
Database UniProt [Online] Accession No. I0LED3, Jun. 13, 2012, pp. 1-2, XP-002743807.
Database Geneseq [Online] Accession No. BAJ28992, Jan. 31, 2013, pp. 1-10, XP-002743803.
Database Geneseq [Online] Accession No. BAJ28991, Jan. 31, 2013, pp. 1-2, XP-002743804.
Database UniProt [Online] Accession No. F4F956, Jun. 28, 2011, pp. 1-2, XP-002743805.
Database UniProt [Online] Accession No. A8LWF7, Dec. 4, 2007, p. 1-2, XP-002743806.
Written Opinion in International Application No. PCT/EP2016/063369, dated Aug. 1, 2016, pp. 1-6.
Written Opinion in International Application No. PCT/EP2016/063373, dated Aug. 8, 2017, pp. 1-7.
Currently pending claims of U.S. Appl. No. 16/302,107, 2018, pp. 1-4.
Okino, S. et al. "Production of D-lactic acid by *Corynebacterium glutamicum* under oxygen deprivation" *Applied Microbiology and Biotechnology*, Jan. 10, 2008, pp. 449-454, vol. 78, No. 3.
Database WPI [Online] Accession No. 2012-K88398, Jan. 27, 2011, pp. 1-2, XP-002759107.
Written Opinion in International Application No. PCT/EP2016/081205, dated Jun. 1, 2017, pp. 1-19.

* cited by examiner

RECOMBINANT YEAST CELLS PRODUCING POLYLACTIC ACID AND USES THEREOF

CROSS-REFERENCE TO RELATED APPLICATION

This application is the U.S. national stage application of International Patent Application No. PCT/EP2016/081205, filed Dec. 15, 2016.

The Sequence Listing for this application is labeled "Seq-List.txt" which was created on Jun. 14, 2018, and is 55 KB. The entire content of the sequence listing is incorporated herein by reference in its entirety.

The present invention relates to recombinant yeast cells having the ability to produce polylactic acid, and to the uses thereof. The present invention further relates to a method for producing polylactic acid with such recombinant yeast cells, and more particularly homopolymers of polylactic acid, as well as to fermentation broths or cell-free extracts of said recombinant yeast cells comprising polylactic acid.

BACKGROUND

Polylactic acid (PLA) is a biodegradable polyester that may be derived from renewable resources such as corn, rice or other sugar- or starch-producing plants. PLA can be easily processed by extrusion, injection, molding, film formation, etc., allowing a large range of applications, particularly for short-term uses (i.e., food packaging, bags, films, etc.). Furthermore, because of the non-toxicity of lactic acid monomers, PLA is one of the most promising biopolymers for medical applications. Due to their excellent biocompatibility and mechanical properties, PLA and their copolymers are becoming widely used in tissue engineering for function restoration of impaired tissues, in drug delivery systems and in various medical implants.

Lactic acid polymers can be synthesized by different processes so as to obtain products with an ample variety of chemical and mechanical properties. More particularly, PLA is mainly synthesized by two methods: the polycondensation of lactic acid (LA), which is carried out in bulk or in solution; or the ring-opening polymerization of lactide (cyclic dimer of lactic acid), which requires catalysts. The direct polycondensation of lactic acid in bulk is not applied on a great scale, because of the competitive reaction of lactide formation and the simultaneously occurring degradation process. The polycondensation of lactic acid in solution gives PLA with molecular weights ranging from the tens to a few hundred thousand g/mol. So far, the synthesis of PLA from lactide is the most effective method of synthesis in industry. However, the use of metal catalysts, cationic catalysts and/or organic catalysts may impact the quality of final product, some catalyst residues being incorporated into the polymer. Moreover, the racemization of part of the lactides during the process may lead to heteropolymers comprising both L-lactic acid and D-lactic acid. In addition this chemical polymerization requires high energetic inputs (heat) that bring additional economic and environmental costs.

Recently, alternative biological processes have been developed, wherein prokaryote cells such as bacteria have been engineered for producing microbial LA-based polyesters. This biological production takes advantage of the enzymatic activity of a polyhydroxyalkanoate (PHA) synthase leading to the production of LA-based polyesters. More precisely, the pathway for utilizing lactyl-CoA as a substrate for the production of LA-based polyesters has been developed in bacteria. However, the main polymer produced by this biological process is a copolymer composed of LA and other PHA (hydroxyacids or hydroxyalkanoate such as 3-hydroxybutyrate) monomers. The resulting copolymers, such as P(3HB-co-LA) have limited mechanical and industrial interest. Furthermore, the PLA polymers generated by this method are amorphous and have a low molecular weight (less than 30,000 g/mol). Such PLA exhibits poor mechanical properties and may not be easily processed in industrial applications such as injection molding, thermoforming or extrusion. Accordingly, such polymer is of low industrial interest.

The present invention describes novel biological methods and microorganisms for producing PLA. The invention allows effective production of homopolymers of PLA with high molecular weight, on large scale.

SUMMARY OF THE INVENTION

The present invention relates to yeast cells engineered to produce PLA and to the uses thereof. More particularly, the invention relates to recombinant yeast cells that exhibit both lactyl-CoA synthase activity and lactyl-CoA polymerase activity and, optionally, an altered lactic acid (LA) metabolism leading to a reduced consumption of LA as carbon source. Consequently, the invention describes the ability of the aforementioned yeast cells to produce high quantities of PLA, and that the PLA produced may be in the form of homopolymers of high molecular weight. The yeast cells compartmentalisation and its membrane-bound organelles are of particular interest for the production of PLA homopolymers essentially devoid of other hydroxyalkanoate monomers. These cells thus allow the design of improved methods of production of PLA with high mechanical properties and broad industrial utilities.

It is therefore an object of the invention to provide recombinant yeast cells comprising a gene encoding a protein having lactyl-CoA synthase activity and a gene encoding a protein having lactyl-CoA polymerase activity, said recombinant cells having the ability of producing polylactic acid (PLA).

In a particular embodiment, the protein exhibiting lactyl-CoA synthase activity is an acyl-CoA transferase, more preferably a propionyl-CoA transferase (Pctp). In another embodiment, the protein exhibiting lactyl-CoA synthase activity is a ligase, such as acyl-CoA ligase.

Preferably, the protein exhibiting lactyl-CoA polymerase activity is a polyhydroxyalkanoate (PHA) synthase.

In a preferred embodiment, the invention relates to recombinant yeast cells expressing at least a gene encoding a protein having lactyl-CoA synthase activity and a gene encoding a protein having lactyl-CoA polymerase activity, and wherein a lactic acid oxidoreductase activity of the yeast is inactivated.

In a particular embodiment, the invention relates to recombinant yeast cells expressing at least a gene encoding a protein having lactyl-CoA synthase activity and a gene encoding a protein having lactyl-CoA polymerase activity, and wherein a lactic acid oxidoreductase activity of the yeast is inactivated, and wherein the 6 acyl-CoA oxidases have been deleted.

In a particular embodiment, the yeast cell is of the genus of *Yarrowia*, preferably *Yarrowia lipolytica*.

The invention also relates to a method for producing PLA comprising
 culturing recombinant yeast cells of the invention in the presence of lactic acid; and optionally
 recovering PLA produced.

A further object of the invention relates to a composition comprising a cell-free extract of the recombinant yeast cells of the invention.

A further object of the invention relates to a composition comprising dried recombinant yeast cells of the invention.

The invention further relates to the use of recombinant yeast cells of the invention for producing PLA and to a method for obtaining PLA and its uses.

The invention is particularly adapted for the production of homo-polylactic acid, especially poly-D-lactic acid (PDLA). In addition, the method described is particularly advantageous for the production of high molecular weight polymer such as PLA, and more especially PDLA, with average molecular weight (Mw) above 40,000 g/mol, such as about 80,000 g/mol.

LEGEND TO THE FIGURES

FIG. 1: Schematic representation of the enzymatic production of polylactic acid using lactic acid and lactyl-CoA as substrates; CoA-SH: Coenzyme A; ACS: acyl-CoA synthase.

Figure 2:
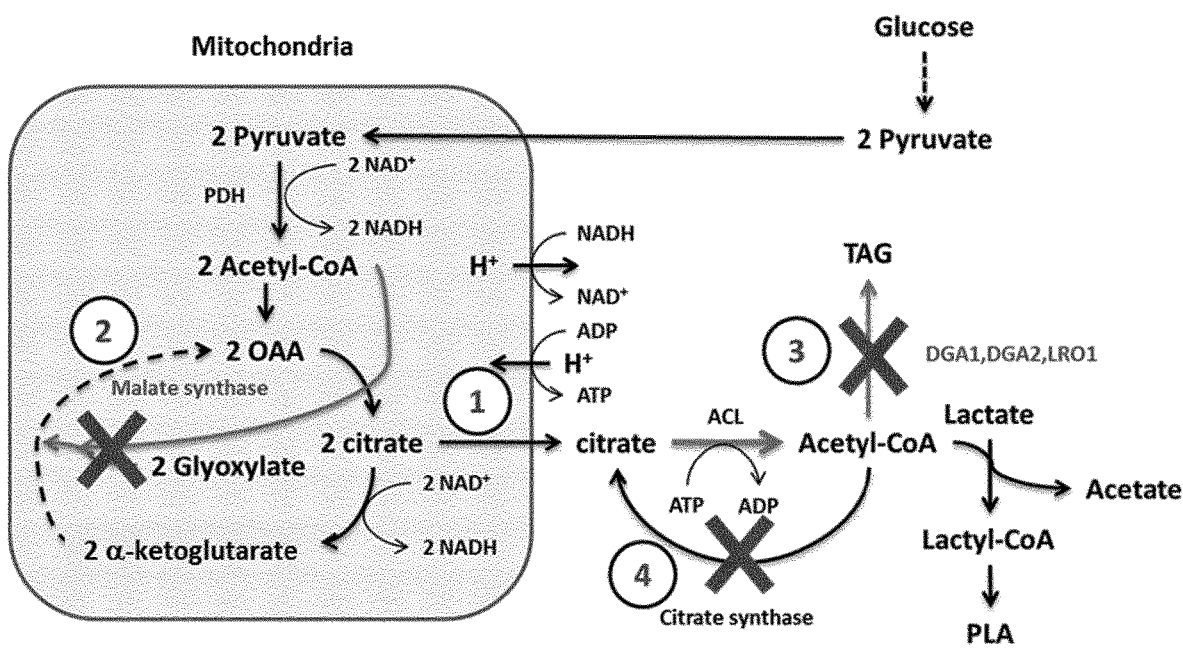

FIG. 2: Depiction of the different metabolic pathways leading to production or consumption of acetyl-CoA in *Y. lipolytica* and are subject of modification; PDH: pyruvate dehydrogenase; OAA: oxaloacetic acid; DGA1, DGA2: acyl-CoA:diacylglycerol acyltransferases; LRO1: phospholipid:diacylglycerol acytransferase.

Figure 3:
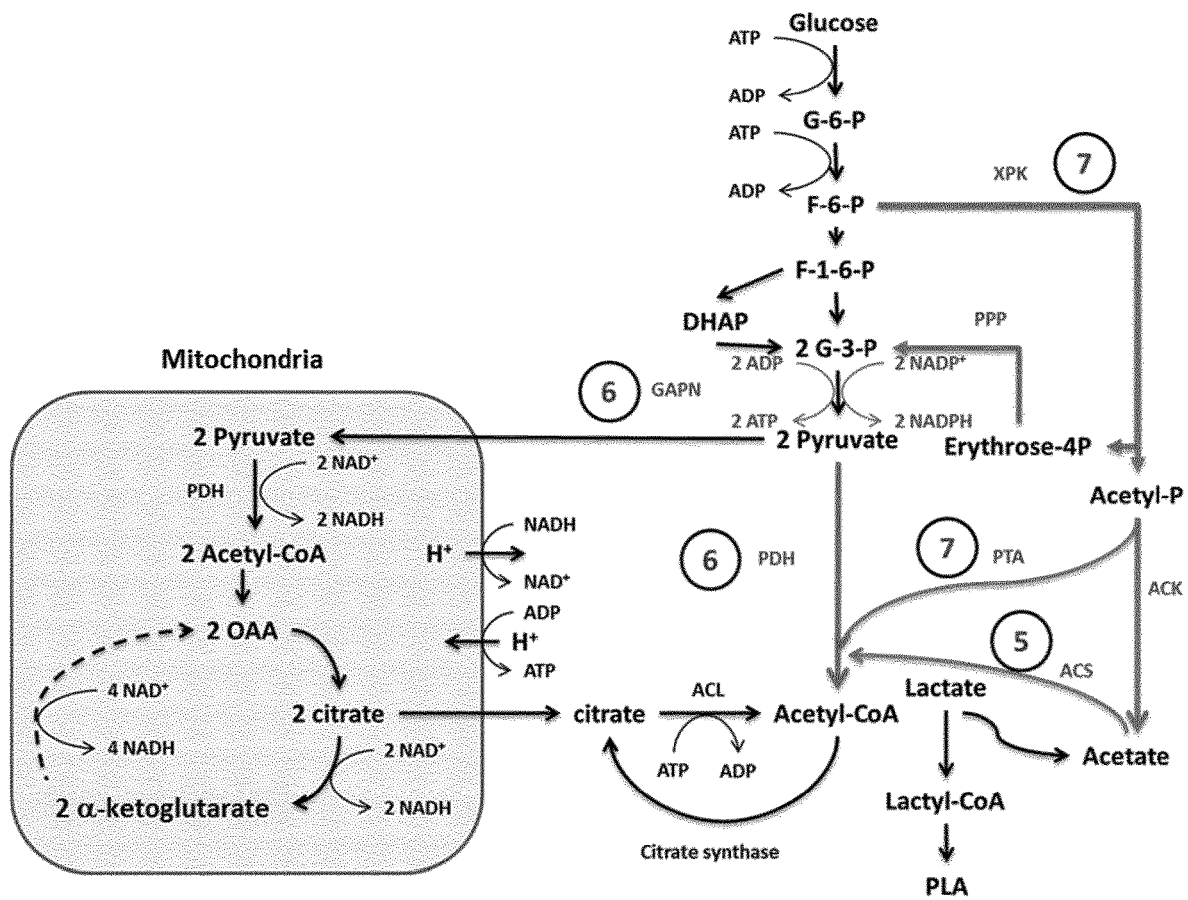

FIG. 3: Schematic representation of the different metabolic pathways that are the subjects of expression in *Yarrowia lipolytica*, for the increase of the cytosolic acetyl-CoA pool. GAPN: glyceraldehyde-3P dehydrogenase; PDH: pyruvate dehydrogenase; PTA: phosphotransacetylase kinase; ACS: acyl-CoA synthetase; ACK: acetate kinase; XPK: phosphoketolase; PPP: pentose phosphate pathway.

Figure 4A:
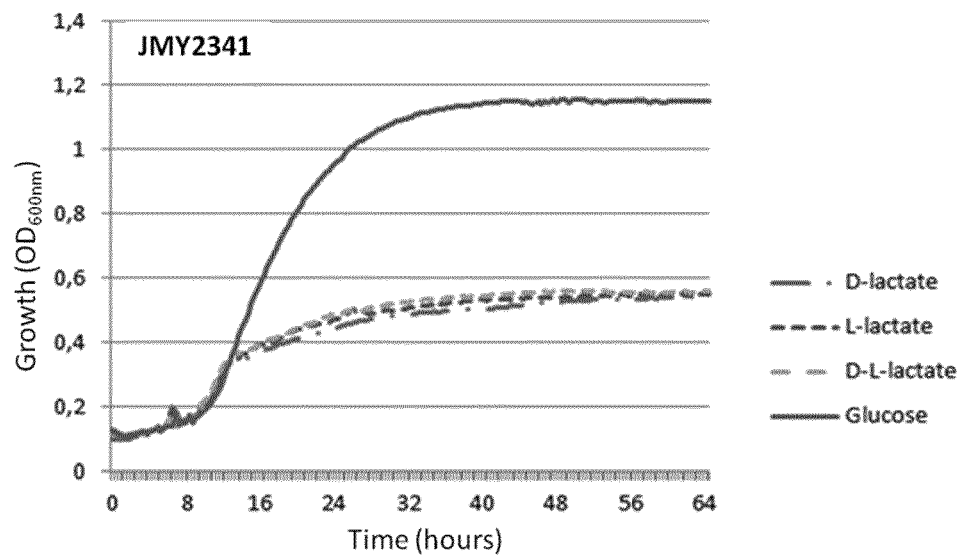
Figure 4B:
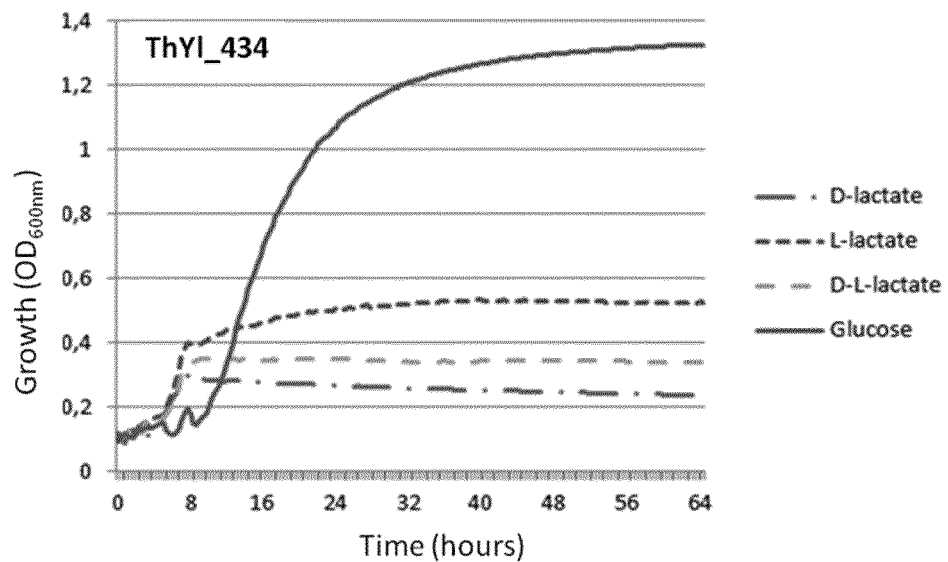

FIG. 4: Growth curve of the control strain JMY2341 (FIG. 4A) and of the lactic acid dehydrogenase Y1DLD1 knockout strain ThY1_434 (FIG. 4B) in media containing lactate or glucose (positive control). The Y1DLD1 disrupted strain is unable to grow on D-lactate and only maintains half of its growth potential ($OD_{600nm}$) on the equimolar racemic mixture of DL-lactate.

Figure 5A:
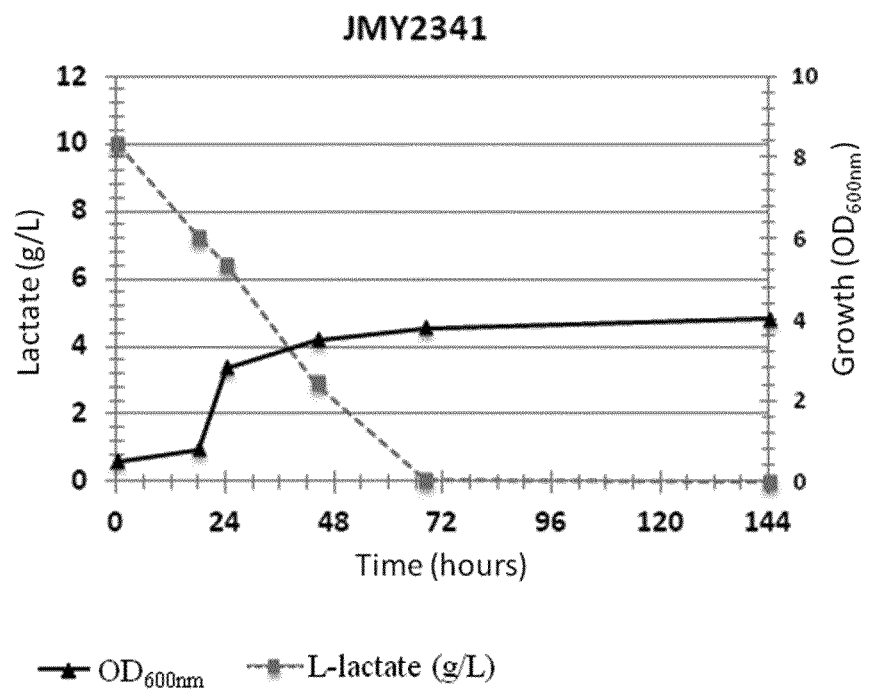
Figure 5B:
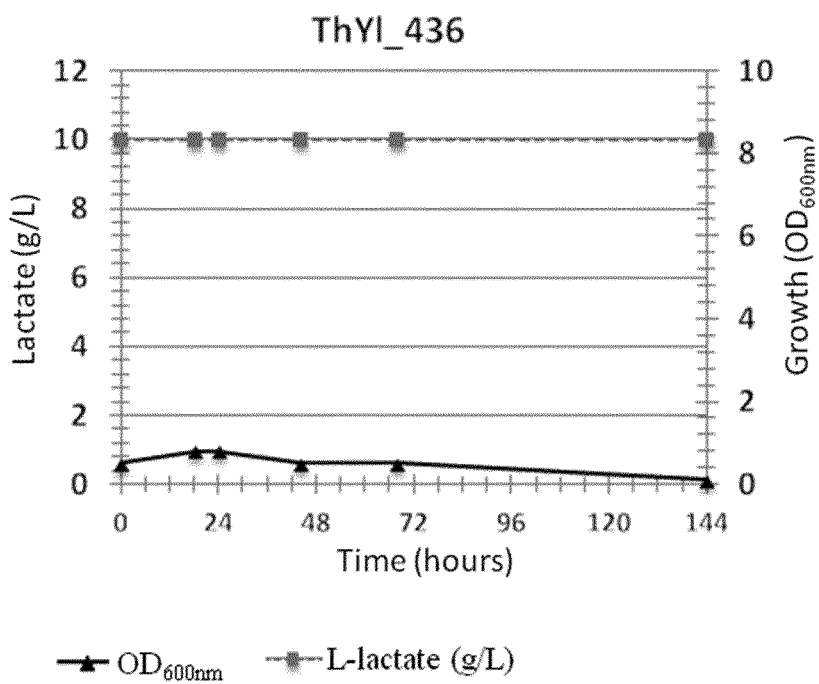

FIG. 5: Growth curve of the control strain JMY2341 (FIG. 5A) and of the lactic acid oxidoreductase Y1CYB21 knockout strain ThY1_436 (FIG. 5B) on L-lactate. The Y1CYB21 knockout strain is unable to grow on L-lactic acid.

Figure 6:
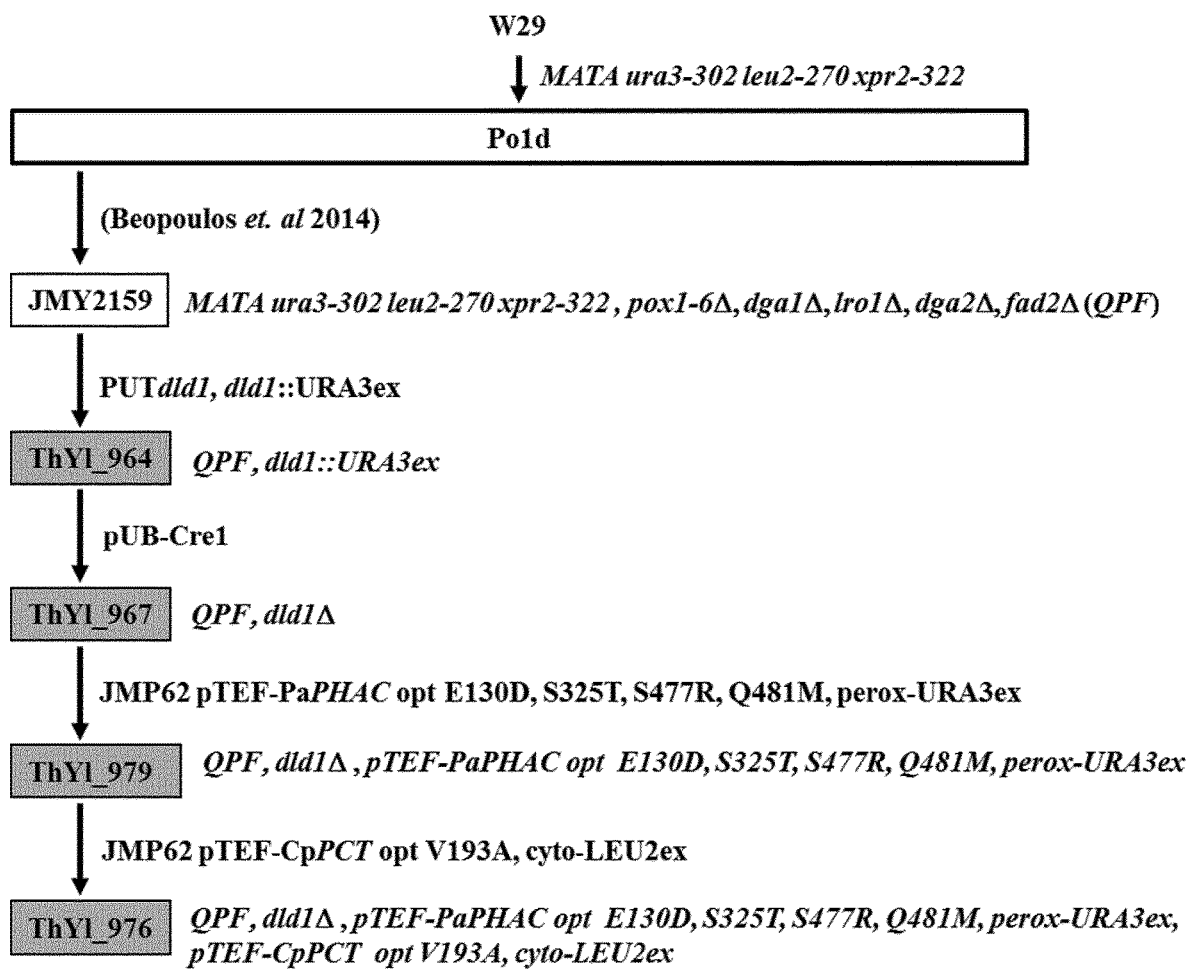

FIG. 6: Schematic illustration of the successive genomic modifications performed in the W29 *Y. lipolytica* wild type strain, according to a particular embodiment.

Figure 7:
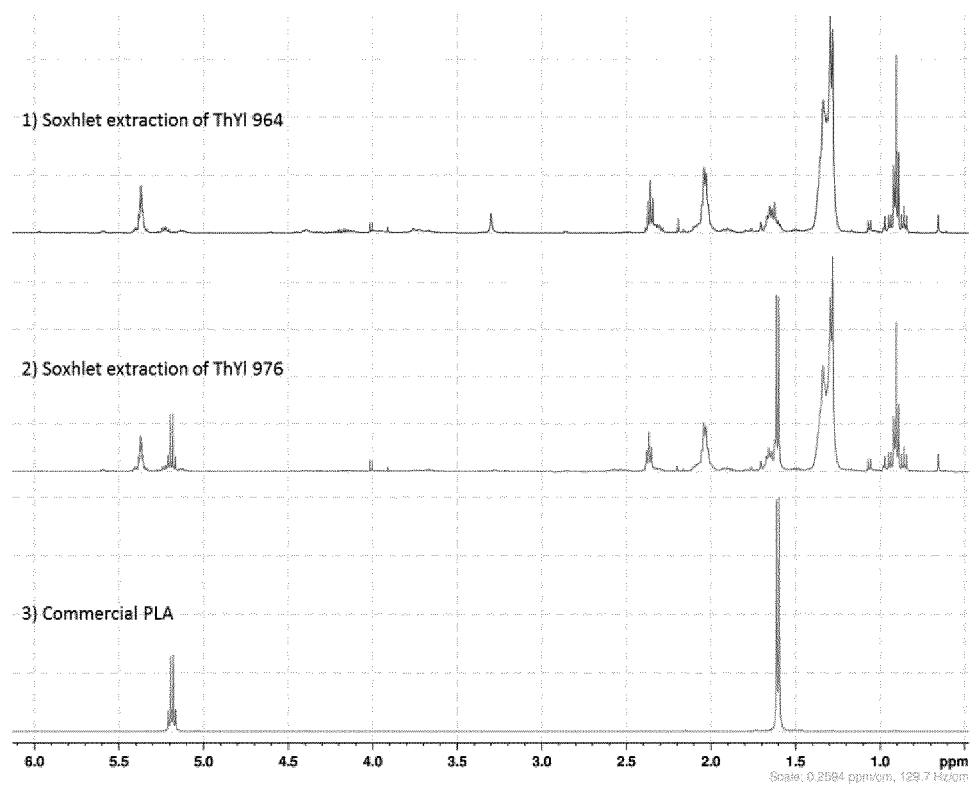

FIG. 7: NMR spectra of: (1) Soxhlet extracted lipid fraction of ThY1_964 control strain dried biomass and (2) Soxhlet extracted lipid fraction of ThY1_976 strain expressing both lactyl-CoA synthase activity and lactyl-CoA polymerase activity dried biomass. The signals between 5.3 and 5.2 ppm, and between 1.7 and 1.5 ppm correspond to the PLA fraction produced by the recombinant yeast cells; (3) Commercial PLA used as control.

Figure 8:
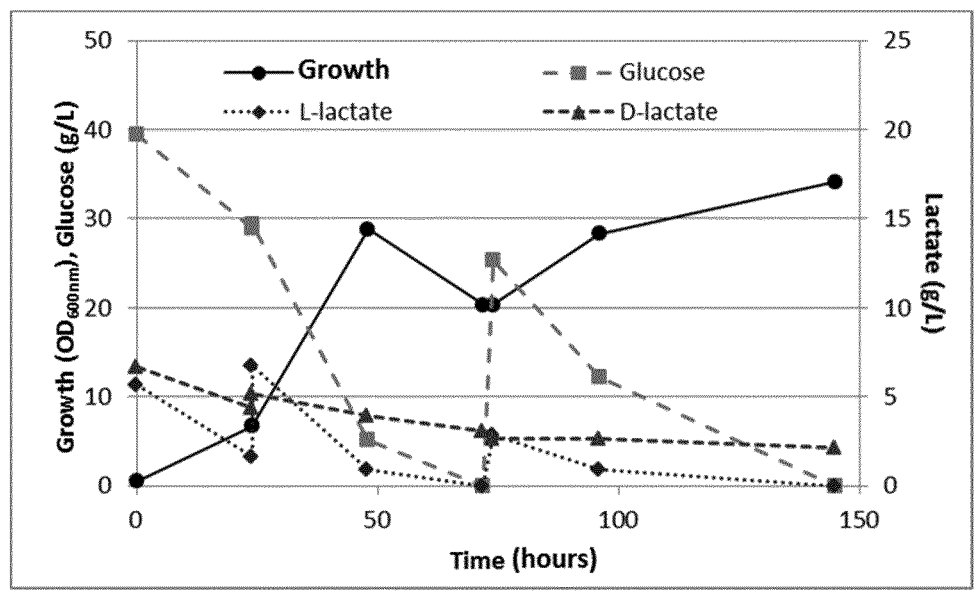

FIG. 8: Biomass evolution and substrate consumption of L-lactate, D-Lactate and Glucose during growth of ThY1_976 recombinant yeast strain.

Figure 9:
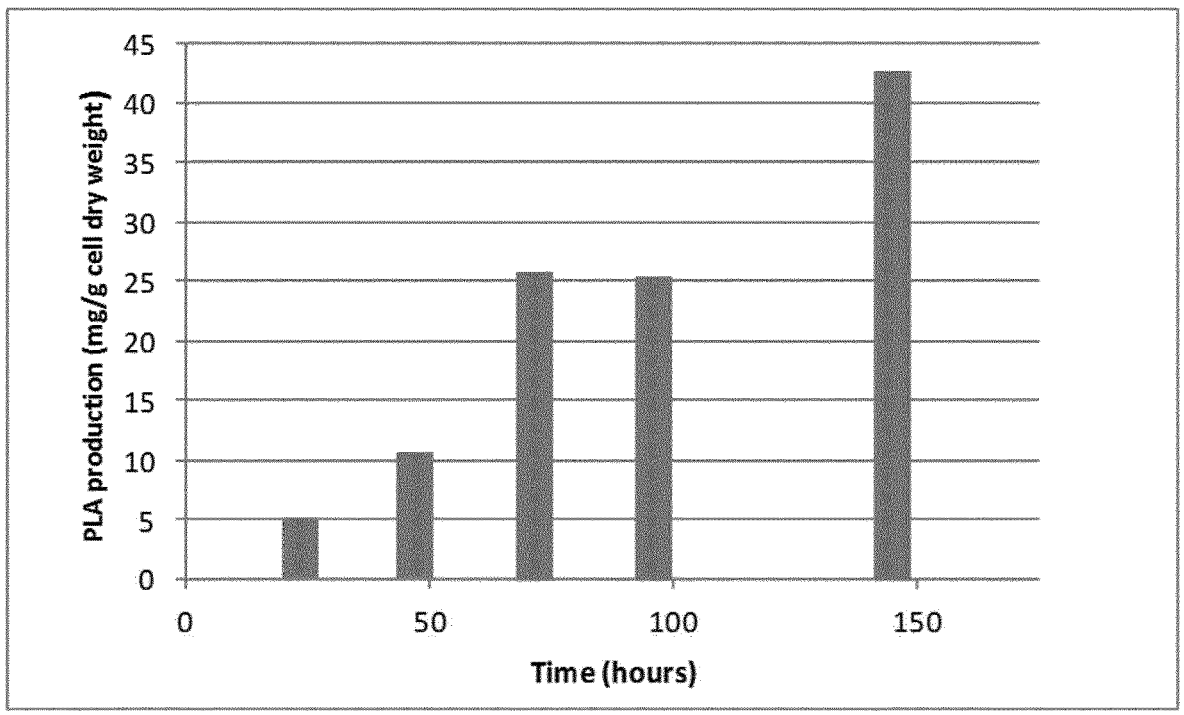

FIG. 9: Graphic representation of PLA production from ThY1_976 recombinant yeast cells during culture.

Figure 10:
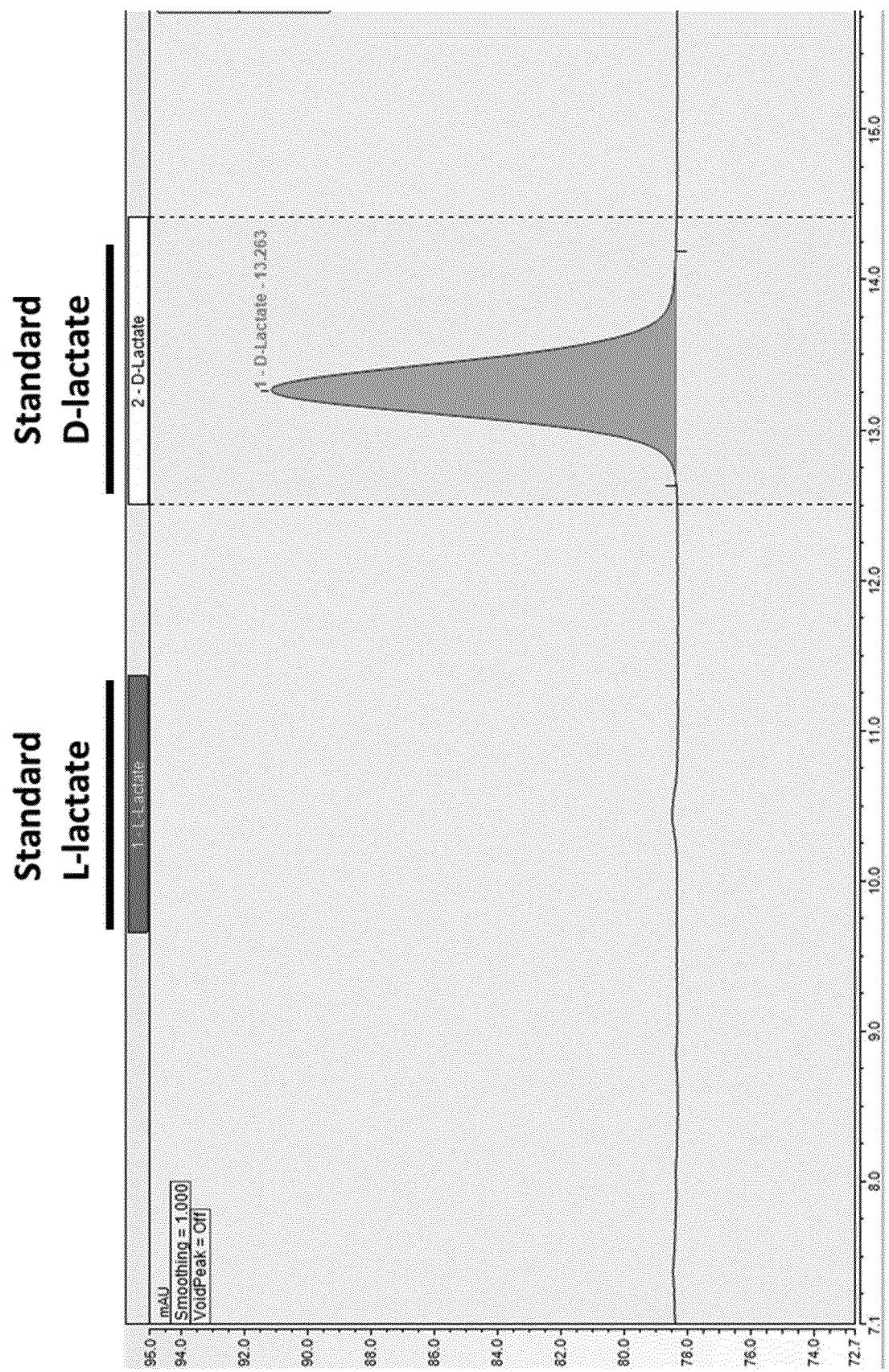

FIG. 10: HPLC chromatogram obtained after complete hydrolysis of PLA extracted from ThY1_976 strain and showing that the PLA produced is a homopolymer exclusively composed of monomers of D-lactic acid.

DETAILED DESCRIPTION OF THE INVENTION

The present invention relates to new recombinant eukaryotic microorganisms engineered for producing polylactic acid. More particularly, the invention relates to recombinant yeast cells, engineered by the inventors, which allow large scale production of high molecular weight (Mw) homopolymers of PLA having remarkable mechanical and physical properties. More particularly, the inventors have discovered that the use of an eukaryotic cell makes it possible to produce PLA homopolymers, devoid of hydroxyalkanoates. Indeed, in yeast there is no free 3-hydroxyalkanoates (3HA) apart from the one under the form of CoA present in the peroxisome. 3HA compounds are produced under the form of ACP (acyl carrier protein) as a transient intermediate during the fatty acid biosynthesis in the confined reaction chambers of the yeast type I fatty acid synthase and thus cannot be liberated in the cytosol and used for polymer production. Said 3HA-CoA production, occurring during the second step of the beta oxidation process, can be abolished by the deletion of the genes encoding the proteins responsible of first or second steps, if PLA homopolymers are produced in the peroxisomes. It is then possible, using yeast cells to produce PLA devoid of other hydroxyalkanoate by producing polymer in a compartment free of them (such as cytosol or mitochondria) or by deleting genes responsible of their synthesis in the peroxisomes. In addition, repurposing yeast organelles, such as peroxisomes and mitochondria, as production compartment can allows to bypass metabolic cross-talk between the engineered PLA pathway and endogenous pathways. An additional advantage using yeasts, such as of *Yarrowia* genus, is their resistance to acidic environment, as the monomer supply could induce a decrease in pH. More importantly, such acidic environment greatly improves the uptake of the monomer and drastically reduces risk of undesirable culture contamination. Moreover, some yeasts such as *Yarrowia lipolytica* are GRAS (Generally Recognized As Safe) microorganisms. They do not produce any endotoxin. PLA can be purified without any contamination by lipopolysaccharides, which is encountered in bacteria and cause immunogenic reactions. Genes that are added to produce the strain of interest are integrated in the genomic chromosome of the yeast and are thus more stable than expression via plasmids as practiced in bacteria. The invention thus provides competitive alternative methods for PLA production that are less expensive and more efficient than chemical processes.

Definitions

The present disclosure will be best understood by reference to the following definitions.

A "polymer" refers to a chemical compound or mixture of compounds whose structure is constituted of multiple units linked by covalent chemical bonds. Within the context of the invention, the term "polymer" includes polymers comprising a single type of repeating unit (i.e., homopolymers) or different types of units (i.e., block copolymers and random copolymers). More particularly, in the context of the invention the terms "homopolymer of PLA" refers to a polymer composed solely either of L- or D-lactic acid units and devoid of any other units (like hydroxyalkanoate or the like). Accordingly, "homopolymers of PLA" designate poly-L- lactic acid (PLLA) or poly-D-lactic acid (PDLA). "Heteropolymers of PLA" designate poly-DL-lactic acid (PDLLA).

In the context of the invention, the terms "lactate" and "lactic acid" are used interchangeably to refer to an organic compound with formula $CH_3CH(OH)CO_2H$ or its ionized form. In absence of further indications, these terms designate indistinctly the L-lactic acid, the D-lactic acid and mixture thereof. In the same way, the terms "polylactate" and "polylactic acid" are used interchangeably to refer to a polyester composed essentially of lactic acid units. In absence of further indication, these terms designate indistinctly PLLA, PDLA and PDLLA.

The terms "nucleic acid", "nucleic sequence," "polynucleotide", "oligonucleotide" and "nucleotide sequence" designate a molecule or sequence of deoxyribonucleotides and/or ribonucleotides.

A "gene" designates any nucleic acid molecule comprising an open reading frame encoding a protein. A gene may contain additional sequences such as a promoter, a transcription terminator, a signal peptide, or an intron, for instance.

The term "recombinant" refers to a nucleic acid construct, a vector, a polypeptide or a cell produced by genetic engineering.

In the present description, a "recombinant yeast cell" refers to a yeast cell that has been genetically modified, most often by insertion of a nucleic acid sequence or unit that did not exist naturally in the existing yeast cell, and/or by inactivation of a native nucleic acid sequence or unit. Said nucleic acid sequence or unit may have been inserted or inactivated in said yeast cell or an ancestor thereof, using recombinant DNA technology or random mutagenesis.

In the context of the invention, the terms "variant" or "mutant" are used for designating a functional protein comprising at least one amino acid modification or alteration, i.e., a substitution, insertion, and/or deletion, at one or more (e.g., several) positions compared to a parent protein (i.e., it is mutated at least at one amino acid position) and that presents the desired properties. The variants may be obtained by various techniques well known in the art. In particular, examples of techniques for altering the DNA sequence encoding the wild-type protein, include, but are not limited to, site-directed mutagenesis, random mutagenesis and synthetic oligonucleotide construction. The term "expression", as used herein, refers to any step involved in the production of a polypeptide including, but being not limited to, transcription, post-transcriptional modification, translation, post-translational modification, and secretion.

In the context of the invention, the "genome of a yeast cell" means all of the genetic material contained in said yeast cell, including the extrachromosomal genetic material contained, for example, in the plasmids, episomes, synthetic chromosomes, etc.

The terms "heterologous sequence" or "heterologous protein" designate a sequence or protein that does not exist in the natural state in the considered microorganism. Conversely, the terms "homologous sequence" and "endogenous sequence", or "homologous protein" and "endogenous protein" designate a sequence or protein that does exist in the natural state in the considered microorganism.

In the same way, the terms "endogenous activity" designates an activity that is present in the natural state in the considered microorganism. Conversely, the terms "exogenous activity" designates an activity that is not present in the natural state in the considered microorganism.

Herein, the terms "peptide", "polypeptide" and "protein" are employed interchangeably and refer to a chain of amino acids linked by peptide bonds, regardless of the number of amino acids forming said chain. The amino acids are herein represented by their one-letter or three-letter code according to the following nomenclature: A: alanine (Ala); C: cysteine (Cys); D: aspartic acid (Asp); E: glutamic acid (Glu); F: phenylalanine (Phe); G: glycine (Gly); H: histidine (His); I: isoleucine (Be); K: lysine (Lys); L: leucine (Leu); M: methionine (Met); N: asparagine (Asn); P: proline (Pro); Q: glutamine (Gln); R: arginine (Arg); S: serine (Ser); T: threonine (Thr); V: valine (Val); W: tryptophan (Trp) and Y: tyrosine (Tyr).

As used therein, the terms "inactivated", "inactivation", "altered" or "defective" in relation with a given activity or protein, indicate a reduction or attenuation in the level of said activity or protein in the yeast cell. Such a reduction is typically of about 20%, more preferably 30%, as compared to a wild-type protein in the yeast cell. Reduction may be more substantial (e.g., above 50%, 60%, 70%, 80% or more), or complete (i.e., knock-out). According to the invention, such inactivation may be obtained by various techniques, performed at the level of DNA, mRNA or protein, to inhibit the expression of the corresponding gene (e.g., transcription or translation) or the activity of the protein. At the level of DNA or mRNA, inactivation may be accomplished by, e.g., deletion, insertion and/or substitution of one or more nucleotides, site-specific mutagenesis, ethyl methanesulfonate (EMS) mutagenesis, targeting induced local lesions in genomes (TILLING), knock-out techniques, or gene silencing using, e.g., RNA interference, antisense, aptamers, and the like. Another particular approach is gene inactivation by insertion of a foreign sequence, e.g., through transposon mutagenesis using mobile genetic elements called transposons, which may be of natural or artificial origin. A protein may also be rendered defective by altering its activity, either by altering the structure of the protein, or by expressing in the cell a ligand of the protein, or an inhibitor thereof, for instance. Preferred inactivation methods affect expression and lead to the absence of production of a functional protein in the yeast cell. In particular, defective gene is obtained by deletion, mutation, insertion and/or substitution of one or more nucleotides.

Biological Polylactic Acid Synthesis

Biological production of PLA may occur in two steps. The first one consists in lactic acid activation in lactyl-CoA using CoA donor. In a particular embodiment, illustrated in FIG. 1, acetyl-CoA is used as the CoA donor. This step requires a lactyl-CoA synthase such as a CoA transferase such as propionyl-CoA transferase (Pctp). In another embodiment, a ligase may be used, such as acyl-CoA ligase that binds CoA on lactic acid in order to form lactyl-CoA.

The second step is the polymerization of lactyl-CoA in PLA by a lactyl-CoA polymerase such as a PHA synthase.

In order to allow biological production of PLA into yeast cells, the inventors have engineered yeast cells that exhibit both lactyl-CoA synthase activity and lactyl-CoA polymerase activity.

According to the invention, the yeasts may naturally exhibit one of these activities and be genetically modified to have the second activity. For instance, the yeast cell originally exhibits lactyl-CoA synthase activity, and a protein having lactyl-CoA polymerase activity has been genetically introduced into the yeast cell or ancestors thereof, or the inverse. Alternatively, the yeast is originally devoid of both activities, and has been genetically modified for these two activities. Alternatively, or in addition, the yeast originally exhibits at least one of these activities, and has been modified so as to promote and/or enhance the expression of the gene(s) involved.

In accordance with the invention, the genome of the yeast cell or of an ancestor thereof has been modified by the introduction of at least one nucleic sequence coding for at least one enzyme involved in the PLA producing pathway, or a biologically active fragment thereof.

In a particular embodiment, the invention provides a recombinant *Yarrowia*, typically a recombinant *Y. lipolytica*, that exhibits an endogenous lactyl-CoA synthase activity, and that is further engineered for expressing a heterologous protein having a lactyl-CoA polymerase activity.

In another embodiment, the invention provides a recombinant *Yarrowia*, typically a recombinant *Y. lipolytica* that has been engineered for expressing both a heterologous protein having lactyl-CoA polymerase activity and a heterologous protein having lactyl-CoA synthase activity.

In a particular embodiment, the protein having lactyl-CoA synthase activity is CoA transferase. Particularly, the protein having CoA transferase activity is a propionyl-CoA transferase (EC:2.8.3.1) known to be able to activate lactic acid in lactyl-CoA.

For instance, a nucleic acid coding for a propionyl-CoA transferase (Pctp) having an amino acid sequence as set forth in SEQ ID No1, SEQ ID No2, SEQ ID No3, SEQ ID No4 or SEQ ID No16, or functional variants thereof having lactyl-CoA synthase activity, has been introduced in the recombinant yeast cell or ancestors thereof.

```
SEQ ID No 1/Pctp Clostridium propionicum
(Accession number Q9L3F7/CAB77207.1)
MRKVPIITADEAAKLIKDGDTVTTSGFVGNAIPEALDRAVEKRFLETG

EPKNITYVYCGSQGNRDGRGAEHFAHEGLLKRYIAGHWATVPALGKMA

MENKMEAYNVSQGALCHLFRDIASHKPGVFTKVGIGTFIDPRNGGGKV

NDITKEDIVELVEIKGQEYLFYPAFPIHVALIRGTYADESGNITFEKE

VAPLEGTSVCQAVKNSGGIVVVQVERVVKAGTLDPRHVKVPGIYVDYV

VVADPEDHQQSLDCEYDPALSGEHRRPEVVGEPLPLSAKKVIGRRGAI

ELEKDVAVNLGVGAPEYVASVADEEGIVDFMTLTAESGAIGGVPAGGV

RFGASYNADALIDQGYQFDYYDGGGLDLCYLGLAECDEKGNINVSRFG

PRIAGCGGFINITQNTPKVFFCGTFTAGGLKVKIEDGKVIIVQEGKQK

KFLKAVEQITFNGDVALANKQQVTYITERCVFLLKEDGLHLSEIAPGI

DLQTQILDVMDFAPIIDRDANGQIKLMDAALFAEGLMGLKEMKS
```

In a particular embodiment, a nucleic acid coding for a variant of the Pctp of SEQ ID No1 comprising preferably at least one of the mutations selected from V193A and A243T and having lactyl-CoA synthase activity is used.

```
SEQ ID No 2/Pctp Aspergillus nidulans
(Accession number Q5B0U7/AN5833.2)
MTHPQQAVHAASLQNPEAFWSHHAQQLHWHKKPSRAIGRSTKTLASGA

SHESWSWFPDGEISTTYNCVDRHVLNGNGDNVAIIWDSAVTGKKEKYT

YRQLLDEVEVLAGVLREEGVKKGDVVIIYMPMIPAALIGALAVARLGA

IHAAVFGGFAAKSLAQRIEAARPRAILTASCGIEGAKGPIAYRPLVEG

AIEASSFKPEKVLIWQRDQLRWNNPDKLGGQRNWNRLVKSARMRGIRA

EPVPVRSTDGLYIIYTSGTTGLPKGVVREAGGHAVGLSLSIKYLFDIH

GPGDTMFCASDIGWVVGHSYILYAPLLVGATTVLFEGKPVGTPDAGTF

WRVVAEHKANVLFTAPTALRAIRKEDPDNKHFEKVAGDNNLRHLRALF

LAGERSEPSIVRAYQDLLTKHAARGALVVDNWWSSESGSPISGLALRS

AVGRVPPRSDEYDVAPLAIRPGSAGLPMPGFDVRVVDDEGNEVAQGTM

GNIVMATPLAPTAFTRLFNDDERFYKGYLKRFGGRWLDTGDAGMIDQD

GYIHVMSRSDDIINVAAHRFSTGQGSIEQAILSHPAIGEASVVGIPDA

LKGHLPFAFITLKQSGGNSPARPSAELFNSVNRLVREQIGAIASLGGM

IQGQGMIPKTRSGKTLRRVLRELVENGARGEFEKEVAVPPTVEDRGVV

EVAREKVREYFESQSGSPKAKL

SEQ ID No 3/Pctp Escherichia coli
(Accession number A0A0F6C4Y4/AFJ29290.1)
MKPVKPPRINGRVPVLSAQEAVNYIPDEATLCVLGAGGGILEATTLIT

ALADKYKQTQTPRNLSIISPTGLGDRADRGISPLAQEGLVKWALCGHW

GQSPRISDLAEQNKIIAYNYPQGVLTQTLRAAAAHQPGIISDIGIGTF

VDPRQQGGKLNEVTKEDLIKLVEFDNKEYLYYKAIAPDIAFIRATTCD

SEGYATFEDEVMYLDALVIAQAVHNNGGIVMMQVQKMVKKATLHPKSV

RIPGYLVDIVVVDPDQSQLYGGAPVNRFISGDFTLDDSTKLSLPLNQR

KLVARRALFEMRKGAVGNVGVGIADGIGLVAREEGCADDFILTVETGP

IGGITSQGIAFGANVNTRAILDMTSQFDFYHGGGLDVCYLSFAEVDQH

GNVGVHKFNGKIMGTGGFIDISATSKKIIFCGTLTAGSLKTEIADGKL

NIVQEGRVKKFIRELPEITFSGKIALERGLDVRYITERAVFTLKEDGL

HLIEIAPGVDLQKDILDKMDFTPVISPELKLMDERLFIDAAMGFVLPE

AAH

SEQ ID No 4/Pctp Ralstonia eutropha
(Accession number Q0K874/CAJ93797.1)
MKVITAREAAALVQDGWTVASAGFVGAGHAEAVTEALEQRFLQSGLPR

DLTLVYSAGQGDRGARGVNHFGNAGMTASIVGGHWRSATRLATLAMAE

QCEGYNLPQGVLTHLYRAIAGGKPGVMTKIGLHTFVDPRTAQDARYHG

GAVNERARQAIAEGKACWVDAVDFRGDEYLFYPSFPIHCALIRCTAAD

ARGNLSTHREAFHHELLAMAQAAHNSGGIVIAQVESLVDHHEILQAIH

VPGILVDYVVVCDNPANHQMTFAESYNPAYVTPWQGEAAVAEAEAAPV

AAGPLDARTIVQRRAVMELARRAPRVVNLGVGMPAAVGMLAHQAGLDG

FTLTVEAGPIGGTPADGLSFGASAYPEAVVDQPAQFDFYEGGGIDLAI

LGLAELDGHGNVNVSKFGEGEGASIAGVGGFINITQSARAVVFMGTLT

AGGLEVRAGDGGLQIVREGRVKKIVPEVSHLSFNGPYVASLGIPVLYI

TERAVFEMRAGADGEARLTLVEIAPGVDLQRDVLDQCSTPIAVAQDLR

EMDARLFQAGPLHL

SEQ ID No 16/Pctp Yarrowia lipolytica
(Accession number XP_505057.1)
SEDHPAIHPPSEFKDNHPHFGGPHLDCLQDYHQLHKESIEDPKAFWKK

MANELISWSTPFETVRSGGFEHGDVAWFPEGQLNASYNCVDRHAFANP

DKPAIIFEADEPGQGRIVTYGELLRQVSQVAATLRSFGVQKGDTVAVY

LPMIPEAIVTLLAITRIGAVHSVIFAGFSSGSLRDRINDAKSKVVVTT
```

-continued
```
DASMRGGKTIDTKKIVDEALRDCPSVTHTLVFRRAGVENLAWTEGRDF

WWHEEVVKHRPYLAPVPVASEDPIFLLYTSGSTGTPKGLAHATGGYLL

GAALTAKYVFDIHGDDKLFTAGDVGWITGHTYVLYGPLMLGATTVVFE

GTPAYPSFSRYWDIVDDHKITHFYVAPTALRLLKRAGTHHIKHDLSSL

RTLGSVGEPIAPDVWQWYNDNIGRGKAHICDTYWQTETGSHIIAPMAG

VTPTKPGSASLPVFGIDPVIIDPVSGEELKGNNVEGVLALRSPWPSMA

RTVWNTHERYMETYLRPYPGYYFTGDGAARDNDGFYWIRGRVDDVVNV

SGHRLSTAEIEAALIEHAQVSESAVVGVHDDLTGQAVNAFVALKNPVE

DVDALRKELVVQVRKTIGPFAAPKNVIIVDDLPKTRSGKIMRRILRKV

LAGEEDQLGDISTLANPDVVQTIIEVVHSLKK
```

In another embodiment, the protein having lactyl-CoA synthase activity is a CoA ligase (EC:6.2.1), preferably an acyl-CoA ligase.

In a particular embodiment, the protein having lactyl-CoA synthase activity is expressed in the cytosol. In another embodiment, the protein having lactyl-CoA synthase activity is expressed in a subcellular organelle, such as the peroxisome or mitochondria. To this end, a nucleic acid coding for the respective targeting sequence may be added at the 5' or 3' terminus of the sequence of interest (see below).

According to the invention, the recombinant yeast cell may express a heterologous protein having a lactyl-CoA polymerase activity.

In a particular embodiment, the protein having a lactyl-CoA polymerase activity is stereospecific. Advantageously, the protein has a D-lactyl-CoA polymerase activity, leading exclusively to the production of PDLA. In another embodiment, the protein has L-lactyl-CoA polymerase activity, leading exclusively to the production of PLLA.

In a particular embodiment, the lactyl-CoA polymerase presents affinity for short chain length acyl-CoA, comprising from 3 to 7 carbons, preferably from 3 to 5 carbons, more preferably 3 carbons, more preferably lactic acid.

In a particular embodiment, the protein having lactyl-CoA polymerase activity is expressed in the cytosol. In another embodiment, the protein having lactyl-CoA polymerase activity is expressed in a subcellular organelle, such as the peroxisome or mitochondria. To this end, a nucleic acid coding for the respective targeting sequence may be added at the 5' or 3' terminus of the sequence of interest (see below).

Preferably, the recombinant yeast cell expresses a heterologous PHA synthase (PhaCp) as lactyl-CoA polymerase.

In a particular embodiment, the PHA synthase is a class II PHA synthase from *Pseudomonas aeruginosa* PAO1 (PaPhaCp).

For instance, the PHA synthase has the amino acid sequence as set forth in SEQ ID No5, or a variant thereof having lactyl-CoA polymerase activity.

```
SEQ ID No 5/PhaC1p of P. aeruginosa PAO1
(Accession number G3XCV5/NP_253743.1)
MSQKNNNELPKQAAENTLNLNPVIGIRGKDLLTSARMVLLQAVRQPLH

SARHVAHFSLELKNVLLGQSELRPGDDDRRFSDPAWSQNPLYKRYMQT

YLAWRKELHSWISHSDLSPQDISRGQFVINLLTEAMSPTNSLSNPAAV
```

```
KRFFETGGKSLLDGLGHLAKDLVNNGGMPSQVDMDAFEVGKNLATTEG

AVVFRNDVLELIQYRPITESVHERPLLVVPPQINKFYVFDLSPDKSLA

RFCLRNGVQTFIVSWRNPTKSQREWGLTTYIEALKEAIEVVLSITGSK

DLNLLGACSGGITTATLVGHYVASGEKKVNAFTQLVSVLDFELNTQVA

LFADEKTLEAAKRRSYQSGVLEGKDMAKVFAWMRPNDLIWNYWVNNYL

LGNQPPAFDILYWNNDTTRLPAALHGEFVELFKSNPLNRPGALEVSGT

PIDLKQVTCDFYCVAGLNDHITPWESCYKSARLLGGKCEFILSNSGHI

QSILNPPGNPKARFMTNPELPAEPKAWLEQAGKHADSWWLHWQQWLAE

RSGKTRKAPASLGNKTYPAGEAAPGTYVHER
```

Alternatively, a nucleic acid coding for a variant of PHA synthase of *P. aeruginosa* PAO1 (SEQ ID No5) comprising preferably at least one of the mutations selected from E130D; S325T; S477R; S477F; Q481M; Q481K; S482G; L484V and A547V, and having lactyl-CoA polymerase activity is used.

In a particular embodiment, the recombinant yeast cell expresses a PHA synthase with the three following mutations in SEQ ID No5: E130D; S477F; Q481K.

In another embodiment, the recombinant yeast cell expresses a PHA synthase with the four following mutations in SEQ ID No5: E130D; S325T; S477R; Q481M (SEQ ID No11 or gene sequence SEQ ID No15).

Alternatively or in addition, a nucleic acid coding for a functional mutant of Class I PHA synthase (EC:2.3.1.B3) such as a mutant of PHA synthase from *R. eutropha*, or a nucleic acid coding for a functional mutant of class III PHA synthase (EC:2.3.1.B4) such as a mutant of PHA synthase from *Chromatium vinosum* may be used (such as SEQ ID No6 or SEQ ID No7).

```
SEQ ID No 6/PhaC1p of R. eutropha H16
(Accession number P23608/CAJ92572.1)
MATGKGAAASTQEGKSQPFKVTPGPFDPATWLEWSRQWQGTEGNGHAA

ASGIPGLDALAGVKIAPAQLGDIQQRYMKDFSALWQAMAEGKAEATGP

LHDRRFAGDAWRTNLPYRFAAAFYLLNARALTELADAVEADAKTRQRI

RFAISQWVDAMSPANFLATNPEAQRLLIESGGESLRAGVRNMMEDLTR

GKISQTDESAFEVGRNVAVTEGAVVFENEYFQLLQYKPLTDKVHARPL

LMVPPCINKYYILDLQPESSLVRHVVEQGHTVFLVSWRNPDASMAGST

WDDYIEHAAIRAIEVARDISGQDKINVLGFCVGGTIVSTALAVLAARG

EHPAASVTLLTTLLDFADTGILDVFVDEGHVQLREATLGGGAGAPCAL

LRGLELANTFSFLRPNDLVWNYVVDNYLKGNTPVPFDLLFWNGDATNL

PGPWYCWYLRHTYLQNELKVPGKLTVCGVPVDLASIDVPTYIYGSRED

HIVPWTAAYASTALLANKLRFVLGASGHIAGVINPPAKNKRSHWTNDA

LPESPQQWLAGAIEHHGSWWPDWTAWLAGQAGAKRAAPANYGNARYRA

IEPAPGRYVKAKA
```

```
SEQ ID No 7/PhaCp of C. vinosum
(Accession number Q402A9)
MEPIDIRPDKLTQEMLDYSRKLGQGMENLLNAEAIDTGVSPKQAVYSE

DKLVLYRYDRPEGAPEAQPVPLLIVYALVNRPYMTDIQEDRSTIKGLL
```

```
-continued
ATGQDVYLIDWGYPDQADRALTLDDYINGYIDRCVDYLREAHGVDKVN

LLGICQGGAFSLMYSALHPDKVRNLVTMVTPVDFKTPDNLLSAWVQNV

DIDLAVDTMGNIPGELLNWTFLSLKPFSLTGQKYVNMVDLLDDPDKVK

NFLRMEKWIFDSPDQAGETFRQFIKDFYQNNGFLNGGVVLGGQEVDLK

DITCPVLNIFALQDHLVPPDASRALKGLTSSPDYTELAFPGGHIGIYV

SGKAQKEVTPAIGKWLNER
```

In a particular embodiment, several copies of a nucleic sequence coding for at least one enzyme involved in the pathway for producing PLA are introduced in the recombinant yeast, particularly, at least two copies.

In a particular embodiment, at least two copies of a nucleic sequence coding for a lactyl-CoA synthase activity, preferably at least two copies of a nucleic sequence coding for a propionyl-CoA transferase, are introduced in the recombinant yeast.

Alternatively or in addition, at least two copies of a nucleic sequence coding for a lactyl-CoA polymerase activity, preferably at least two copies of a nucleic sequence coding for a PHA synthase, are introduced in the recombinant yeast.

In a preferred embodiment, at least two copies of a nucleic sequence coding for a propionyl-CoA transferase and at least two copies of a nucleic sequence coding for a PHA synthase are introduced in the recombinant yeast.

Advantageously, the nucleic sequence(s) introduced in the recombinant yeast is (are) under the control of an inducible or constitutive promoter. Particularly, promoters with different strength are used to control the expression of at least one enzyme. As an example, promoters TEF and 4UAS-TEF are used to control the expression of the nucleic sequences. Preferably, the nucleic sequence coding for a propionyl-CoA transferase and the nucleic sequence coding for a PHA synthase are under the control of the 4UAS-TEF promoter.

It is therefore an object of the invention to provide a recombinant yeast cell, preferably a recombinant *Yarrowia*, typically a recombinant *Y. lipolytica* that has been engineered for expressing both at least one Pctp having the amino acid sequence as set forth in SEQ ID No1, SEQ ID No2, SEQ ID No3, SEQ ID No4, SEQ ID No16, or a variant thereof, and at least one PhaCp having the amino acid sequence as set forth in SEQ ID No5, SEQ ID No6, SEQ ID No7 or SEQ ID No11, or a variant thereof.

Protein Targeting in Subcellular Organelles

In a particular example, the production of PLA may be confined into specific subcellular organelles of the recombinant yeast cell, such as mitochondria or peroxisome, rather than the cytosol. Such confined production may be useful for favoring the production of PLA with high molecular weight.

The activities required for the PLA production, and the associated proteins, must then be targeted into the subcellular organelle of interest. To this end, specific sequences allowing protein targeting may be added at the 5' or 3' terminus of the nucleic acid coding for the proteins of interest.

In a particular embodiment, the PLA production may be confined into peroxisome, by using a Peroxisome Targeting Sequence (PTS) with the proteins that are not expressed or targeted naturally into the peroxisome.

For instance, a nucleic acid coding for a PTS as set forth in SEQ ID No8 (PTS1), which corresponds to 14 successive amino acids of the isocitrate dehydrogenase (YALI0C16885p/P41555—Ic11p Isocitrate lyase from *Y. lipolytica*) may be used. In another embodiment, the PTS may correspond to a tripeptide such as SKL or AKL or any sequence known by a person skilled in the art. Preferably, the PTS is located at the C-terminus of the protein of interest. In another embodiment, the PTS sequence consists on the N-terminus of the *Y. lipolytica* thiolase (YALI0E18568p/Q05493—Pot1p 3-ketoacyl-CoA thiolase) which is cleaved upon peroxisome entry (SEQ ID No9—PTS2). PTS2 is preferably located at the N-terminus of the protein of interest. More generally speaking, any PTS known by the person skilled in the art may be used.

```
SEQ ID No 8:
MGAGVTEDQFKSKL

SEQ ID No 9:
MDRLNNLATQLEQNPA
```

It is therefore an object of the invention to provide a recombinant yeast cell, preferably a recombinant *Yarrowia*, typically a recombinant *Y. lipolytica* that has been engineered for expressing at least one Pctp having the amino acid sequence as set forth in SEQ ID No1, SEQ ID No2, SEQ ID No3, SEQ ID No4, SEQ ID No16, or a variant thereof, in cytosol and at least one PhaCp having the amino acid sequence as set forth in SEQ ID No5, SEQ ID No6, SEQ ID No7 or SEQ ID No11, or a variant thereof in peroxisome. In a particular embodiment, the amino acid sequence of the PhaCp further comprises at its C-terminus the amino acid sequence set forth in SEQ ID No8 or at its N-terminus the amino acid sequence set forth in SEQ ID No9.

Alternatively, the PLA production may be confined into mitochondria, and more particularly into mitochondrial matrix or mitochondrial intermembrane space, by attaching a Mitochondrial Targeting Sequence (MTS) to the proteins that are not expressed or targeted naturally into the mitochondria. In a particular embodiment, a nucleic acid coding for the MTS as set forth in SEQ ID No10 may be used, that corresponds to 26 successive amino acids of the malic enzyme (YALI0E18634p/Q6C5F0—Mae1p). This MTS is preferably added at the N-terminus of the protein of interest. More generally speaking, any MTS known by the person skilled in the art may be used.

```
SEQ ID No 10:
MLRLRTMRPTQTSVRAALGPTAAARN
```

Lactic Acid Metabolism

According to the invention, the ability of the yeast cell to consume lactic acid as a carbon source may be attenuated or inhibited. Accordingly, the recombinant yeast cell will be solely able to polymerize LA for producing PLA. That may be of particular interest with *Y. lipolytica* or *Saccharomyces cerevisiae* that usually consume lactic acid as a carbon source.

To this end, the yeast cell may be modified in order to inactivate its lactic acid degradation pathway. For instance at least one endogenous lactic acid oxidoreductase responsible of converting lactic acid to pyruvate is inactivated.

In the context of the invention, the expression "lactic acid oxidoreductase" is used to designate any enzyme able to produce pyruvate from lactate, and the reverse (EC:1.1.1.27, EC:1.1.1.28, EC:1.1.2.3, EC:1.1.2.4). More particularly, this expression encompasses lactate dehydrogenase, ferricytochrome, flavocytochrome, and cytochrome oxidoreductase.

Preferably, a D-lactic acid dehydrogenase, that converts D-lactic acid to pyruvate, is inactivated. In a particular embodiment, an endogenous L-lactic acid cytochrome b2 or c oxidoreductase may be maintained, so that the yeast remains able to degrade L-lactic acid. D-lactic-acid (D-LA) stays available for the synthesis of PLA. Such recombinant yeast cell may advantageously be able to produce PDLA.

Alternatively, an endogenous L-lactic acid oxidoreductase is inactivated, whereas an endogenous D-lactic acid oxidoreductase is maintained, so that the yeast remains able to degrade D-lactic acid. L-lactic-acid (L-LA) stays available for the synthesis of PLA. Such recombinant yeast cell may advantageously be able to produce PLLA.

Alternatively, both endogenous D-lactic acid and L-lactic acid oxidoreductases may be inactivated so that D-lactic-acid (D-LA) and L-lactic-acid (L-LA) both stay available for the synthesis of PLA. Such recombinant yeast cell may advantageously be able to produce PDLLA.

In a particular embodiment, D-lactic acid oxidoreductase is D-lactic acid dehydrogenase (DLD), preferably from the protein families GL3C0735 or GL3C0514, such as Dld1p, Dld2p and Dld3p. In another particular embodiment, the L-lactic acid oxidoreductase is cytochrome oxidoreductase (CYB), preferably from the protein family GL3C0472, such as Cyb2p, Cyb21p and Cyb22p.

Table 1 and Table 2, below, list four putative lactic acid oxidoreductases from *Y. lipolytica* and *S. cerevisiae* respectively and their predicted localisation.

TABLE 1

Putative lactic acid oxidoreductases of *Y. lipolytica*

| Name | Family | Protein | Putative function | Accession number | Predicted localisation |
|---|---|---|---|---|---|
| YlDLD1 | GL3C0735 | YALI0E03212p | D-lactate dehydrogenase | Q6C773 | Mitochondria |
| YlDLD2 | | YALI0C06446p | | Q6CCU5 | |
| YlCYB21 | GL3C0472 | YALI0D12661p | L-lactic acid cytochrome b2 oxidoreductase | Q6C9A7 | Peroxisome |
| YlCYB22 | | YALI0E21307p | | Q6C538 | |

TABLE 2

Putative lactic acid oxidoreductases of *S. cerevisiae*.

| Name | Family | Protein | Putative function | Accession number | Localisation |
|---|---|---|---|---|---|
| ScDLD1 | GL3C0514 | SACE0D01650p | D-lactate dehydrogenase | P32891 | Mitochondria |
| ScDLD2 | GL3C0735 | SACE0D01562p | | P46681 | |
| ScDLD3 | | SACE0E00242p | | P39976 | Cytoplasm |
| ScCYB2 | GL3C0472 | SACE0M01892p | L-lactate cytochrome b2 oxidoreductase | P00175 | Mitochondria |

In a particular embodiment, the invention provides a recombinant *Y. lipolytica* wherein YlDld1p has been inactivated.

In another particular embodiment, the invention provides a recombinant *Y. lipolytica* wherein YlCyb21p has been inactivated.

It is therefore an object of the invention to provide a recombinant *Y. lipolytica* that has been engineered for expressing at least one Pctp having the amino acid sequence as set forth in SEQ ID No1, SEQ ID No2, SEQ ID No3, SEQ ID No4, SEQ ID No16, or a variant thereof, in cytosol, at least one PhaCp having the amino acid sequence as set forth in SEQ ID No5, SEQ ID No6, SEQ ID No7 or SEQ ID No11, or a variant thereof and further comprising at its C-terminus the amino acid sequence set forth in SEQ ID No8 or at its N-terminus the amino acid sequence set forth in SEQ ID No9 in order to be addressed in the peroxisome, and that has been further engineered in order to inactivate the lactate dehydrogenase (YlDld1p and/or YlCyb21p).

Alternatively, the inventors have discovered that no D-lactate oxidoreductase activity is observed by culturing the recombinant yeast cell in a medium devoid of particular amino acids. For instance, *Y. lipolytica* may be cultured in a culture media devoid of Ala, Arg, Asn, Gln, Be, Leu, Lys, Phe, Pro, Thr and Val to avoid the expression of YlDld1p.

Alternatively, it is possible to inhibit or reduce the consumption of lactic acid by providing other suitable carbon sources to the yeast cell.

In order to improve lactic acid transport into the yeast cells or to reduce its export out of the yeast cells, the cells may be partially inactivated for export or improved for import, preferably D-lactic transport/export.

For instance, the intake of lactic acid into the cells can be increased by overexpressing or overactivating lactate importers, such as specific membrane transporters. Alternatively or in addition, the export of lactic acid out of the cells can be at least reduced by inactivation or deletion of lactic acid exporters.

In an embodiment, the recombinant yeast cell exhibits an exogenous lactic acid racemase activity. For instance, the racemase converts L-lactate into D-lactate or the reverse. In a particular embodiment, the recombinant yeast cell comprises the racemase from *Lactobacillus plantarum* (LpLarAp—EC:5.2.2.1—M4KDH2/AGE37852).

Modified Cytosolic Acetyl-CoA Metabolism

According to the invention, the recombinant yeast cell exhibits lactyl-CoA synthase activity to produce lactyl-CoA from lactic acid. In a particular embodiment, lactyl-CoA synthase activity is performed using a Pctp, which uses acetyl-CoA as CoA donor.

In this context, the production of PLA in the cytosol may be facilitated by enhancing acetyl-CoA availability into the cytosol of the recombinant yeast cells. To this end, three alternative or cumulative ways may be considered: redirecting part of the acetyl-CoA (in majority contained in the mitochondria of yeast cells) from the mitochondria to the cytosol; altering the metabolic pathways that use acetyl-CoA in the cytosol; introducing new metabolic pathways in order to increase cytosolic acetyl-CoA production (FIG. 2 and FIG. 3).

Some yeasts, such as *Y. lipolytica*, may use cytosolic acetyl-CoA for the synthesis of triacylglycerol (TAG). In such case, TAG production is directly in competition with PLA production. Thus, according to a preferred embodiment, the recombinant yeast cell may be modified to inactivate the TAG synthesis pathway. For instance, in *Y. lipolytica*, the genes Y1DGA1 (YALI0E32769g/XM_504700.1) and/or Y1DGA2 (YALI0F06578g/XM_505086.1) and/or Y1LRO1 (YALI0E16797g/XM_504038.1), encoding endogenous diacylglycerol-transferases (Beopoulos et al., 2008) may be inactivated (FIG. 2 point 3).

In addition, some yeasts, such as *Y. lipolytica*, also possess a gene encoding for a citrate synthase (EC:2.3.3.16) that performs the reverse reaction of the one catalyzed by the ATP citrate lyase. Such reaction consumes cytosolic acetyl-CoA and is directly in competition with PLA production. Accordingly, in another preferred embodiment, citrate synthase activity is inactivated in the recombinant yeast cell (FIG. 2, point 4).

In addition, in some yeast cells, such as *Y. lipolytica*, most of the cytosolic acetyl-CoA pool comes from the conversion of citrate, produced through the Krebs cycle, into acetyl-CoA by ATP citrate lyase (EC:2.3.3.8). A transmembrane transport mechanism couples malate import to export citrate out of the mitochondria. Accordingly, in a particular embodiment, the recombinant yeast cell of the invention is cultivated under particular conditions that induce a physiological state favorable for citrate export to the cytosol (see FIG. 2, point 1). For instance, the culture medium is at least temporarily restricted in specific nutrient(s), such as nitrogen, phosphate and/or oxygen.

Alternatively or in addition, malate synthase activity (EC:2.3.3.9) that drives part of the mitochondrial acetyl-CoA away from citrate production as to be used for malate production (glyoxylate shunt pathway) may be inactivated or attenuated (FIG. 2, point 2).

In a particular embodiment, a gene encoding a citrate synthase and/or a gene encoding a malate synthase is inactivated in the recombinant yeast cell of the invention, or ancestor thereof.

In another embodiment, the recombinant yeast cell exhibits an inactivated acyl-CoA:diacylglycerol acyltransferase (DGAT1/2, DGA1/2) and/or phospholipid:diacylglycerol acyltransferase (PDAT, LRO1) activity.

As well illustrated in FIG. 1, the reaction catalyzed by the Pctp produces acetate in addition to lactyl-CoA. In a particular embodiment, in order to increase the cytosolic production of acetyl-CoA, a heterologous gene coding for an acetyl-CoA synthase also called Acsp (EC:6.2.1) may be introduced in the recombinant yeast cell to convert the acetate back into acetyl-CoA. Alternatively, an endogenous gene coding for an acetyl-CoA synthase can be overexpressed. This reaction can be ADP or AMP dependent according to the enzyme considered (FIG. 3, point 5). Accordingly, in a particular embodiment, the recombinant yeast cell further comprises a gene encoding an acetyl-CoA synthase.

In the same way, a heterologous pyruvate dehydrogenase may be introduced in the recombinant yeast cell for the conversion of glycolytic pyruvate into acetyl-CoA in the cytosol (FIG. 3, point 6). An enzyme with low sensitivity to high NADH/NAD$^+$ ratio is preferably used, such as the EfPdhp (NP_815074.1, NP_815075.1, NP_815076.1, NP_815077.1) from *Enterococus faecalis* or any other enzyme known by the person skilled in the art. NADH/NAD$^+$ ratio in the cytosol could also be modulated by introduction of a gene coding for a non-phosphorylating glyceraldehyde-3P dehydrogenase that allows generation of NADPH during glycolysis instead of NADH (FIG. 3, point 6). Accordingly, in a particular embodiment, the recombinant yeast cell further comprises a gene encoding a pyruvate dehydrogenase, said pyruvate dehydrogenase being expressed at least in the cytosol of the recombinant cell.

Alternatively or in addition, an alternative pathway for cytosolic acetyl-CoA production may be introduced in the yeast cell, by the heterologous expression of a phosphoketolase (EC:4.1.2.22). Phosphoketolase catalyzes the formation of acetyl-P and erythrose-4P from fructose-6P (Meile et al., 2001). In this metabolic pathway, acetyl-P is converted into acetyl-CoA by the action of a phosphotransacetylase (EC:2.3.1.8) or by the combined action of an acetate kinase (EC:2.7.2.1) and an acetyl-CoA synthase. Erythrose-4P undergoes carbon rearrangement by the action of transketolase and transaldolase activities, both intrinsically expressed in the pentose phosphate pathway of *Y. lipolytica* and thus is made capable of entering glycolysis. In addition, introduction of a gene coding for an heterologous fructose-1-6-biphosphatase (EC:3.1.1.11) allows a complete recycling of erythrose-4P that gives the possibility to convert 100% of the carbon present in the substrate into acetyl-CoA without $CO_2$ production (FIG. 3, point 7).

Recombinant Yeast Cell

It is an object of the invention to provide a recombinant yeast cell exhibiting lactyl-CoA synthase activity, preferably a CoA transferase activity and a lactyl-CoA polymerase activity, and that is able to produce PLA.

Advantageously, the selected yeast cell is originally able to produce and accumulate high concentration of lipids. In a particular embodiment, the yeast cell is selected from GRAS (Generally Regarded As Safe) yeasts. In addition, the selected yeast is advantageously able to grow at low pH.

According to the invention, the yeast cell preferably belongs to *Yarrowia, Saccharomyces, Kluyveromyces, Candida, Pichia, Schizosaccharomyces, Zygosaccharomyces, Hansenula, Trichosporon, Yamadazyma, Cryptococcus, Lipomyces, Rhodosporidium, Rhodotorula, Geotrichum, Kloeckera, Schwanniomyces, Brettanomyces, Debaryomyces* or *Issatchenkia* genus.

In a particular embodiment, the yeast cell is a *Yarrowia* selected from the group consisting of *Yarrowia bubula, Yarrowia deformans, Yarrowia lipolytica, Yarrowia yakushimensis, Yarrowia galli, Yarrowia oslonensis, Yarrowia hollandica, Yarrowia phangngensis, Yarrowia alimentaria*, and *Yarrowia porcina*, preferably *Yarrowia lipolytica*.

It is therefore an object of the invention to provide a recombinant *Y. lipolytica* expressing a heterologous Pctp, and a heterologous PhaCp.

In a particular embodiment, the recombinant *Yarrowia lipolytica* expresses a Pctp having an amino acid sequence as set forth in SEQ ID No 1, SEQ ID No 2, SEQ ID No 3, SEQ ID No 4, or SEQ ID No 16 or functional variants thereof having lactyl-CoA synthase activity.

In a particular embodiment, the recombinant *Y. lipolytica* expresses a PhaCp having an amino acid sequence as set forth in SEQ ID No5, or a functional variant thereof having lactyl-CoA polymerase activity, comprising preferably at least one mutation selected from E130D, S325T, S477F, S477R, Q481K Q481M, S482G, L484V and A547V, or as set forth in SEQ ID No6 or SEQ ID No7.

Advantageously, a lactic acid oxidoreductase activity of the recombinant *Y. lipolytica* has been inactivated. In a particular embodiment, at least Y1Dld1p has been inactivated, so that the degradation pathway of D-lactic acid is suppressed or at least attenuated.

In a particular embodiment, the recombinant *Y. lipolytica* expresses a quadruple variant of PhaC1p from *P. aeruginosa* (SEQ ID No11) and a functional variant of the Pctp from *C. propionicum* (SEQ ID No1) with the mutation V193A.

SEQ ID No 11/PhaC1p from *P. aeruginosa* PA01
with mutations E130D, S325T, S477R and Q481M
MSQKNNNELPKQAAENTLNLNPVIGIRGKDLLTSARMVLLQAVRQPLH

SARHVAHFSLELKNVLLGQSELRPGDDDRRFSDPAWSQNPLYKRYMQT

YLAWRKELHSWISHSDLSPQDISRGQFVINLLTDAMSPTNSLSNPAAV

KRFFETGGKSLLDGLGHLAKDLVNNGGMPSQVDMDAFEVGKNLATTEG

AVVFRNDVLELIQYRPITESVHERPLLVVPPQINKFYVFDLSPDKSLA

RFCLRNGVQTFIVSWRNPTKSQREWGLTTYIEALKEAIEVVLSITGSK

DLNLLGACSGGITTATLVGHYVASGEKKVNAFTQLVTVLDFELNTQVA

LFADEKTLEAAKRRSYQSGVLEGKDMAKVFAWMRPNDLIWNYWVNNYL

LGNQPPAFDILYWNNDTTRLPAALHGEFVELFKSNPLNRPGALEVSGT

PIDLKQVTCDFYCVAGLNDHITPWESCYKSARLLGGKCEFILSNRGHI

MSILNPPGNPKARFMTNPELPAEPKAWLEQAGKHADSWWLHWQQWLAE

RSGKTRKAPASLGNKTYPAGEAAPGTYVHER

As exposed above, if required, all or part of the heterologous sequences expressed in the recombinant yeast cell may contain a PTS or a MTS in order to be addressed into the peroxisome or mitochondria of the cell. In the case where a targeting signal peptide is already present in the sequence, it could be deleted and/or changed for the protein to be addressed in the desired compartment. Particularly, the recombinant yeast cell expresses a heterologous Pctp addressed to cytosol, and a heterologous PhaCp addressed to peroxisome.

In a particular embodiment, the recombinant yeast cell has been deleted for diacylglycerol transferases to avoid TAG (triacylglycerol) production. Accordingly, the present invention provides a recombinant *Yarrowia*, wherein at least one of the genes selected from Y1LRO1, Y1DGA1 and Y1DGA2 have been deleted.

In another particular embodiment, the recombinant yeast cell has been deleted for the 6 acyl-CoA oxidases (Y1POX1: YALI0E32835g/XM_504703.1, Y1POX2: YALI0F10857g/XM_505264.1, Y1POX3: YALI0D24750g/XM_503244.1, Y1POX4: YALI0E27654g/XM_504475.1, Y1POX5: YALI0C23859g/XM_502199.1, Y1POX6: YALI0E06567g/XM_503632.1), preventing beta-oxidation (genotype: pox1-6Δ) to avoid incorporation of beta-oxidation derived 3-hydroxy-acyl-CoA. This deletion may be useful for the production of homopolymer of PLA in peroxisome.

It is therefore an object of the invention to provide a recombinant *Y. lipolytica* that has been engineered for expressing at least one Pctp having the amino acid sequence as set forth in SEQ ID No1, SEQ ID No2, SEQ ID No3, SEQ ID No4, SEQ ID No16, or a variant thereof, in cytosol, at least one PhaCp having the amino acid sequence as set forth in SEQ ID No5, SEQ ID No6, SEQ ID No7 or SEQ ID No11, or a variant thereof and further comprising at its C-terminus the amino acid sequence set forth in SEQ ID No8 or at its N-terminus the amino acid sequence set forth in SEQ ID No9 in order to be addressed in the peroxisome, and that has been further engineered in order to inactivate both the lactate dehydrogenase (Y1Dld1p and/or Y1Cyb21p) and the acyl-CoA oxidases (Y1POX1, Y1POX2, Y1POX3, Y1POX4, Y1POX5, Y1POX6).

In a particular embodiment, the recombinant yeast cell may further express amphiphilic proteins capable of forming micro-compartments that encapsulate and thereby isolate the PLA produced. For instance, the recombinant yeast cell may be further engineered to express phasins that arrange in micro-compartments encapsulating the PLA produced.

In a particular embodiment, the recombinant yeast cell expresses may express a phasine protein as set forth in SEQ No17 or SEQ No18. These proteins may contain no peptide signal, a PTS or a MTS in order to be addressed to cytosol, peroxisomes or mitochondria respectively. For instance, PTS as set forth in SEQ ID No8 or SEQ ID No9 may be used. For instance, MTS as set forth in SEQ ID No10 may be used.

SEQ ID No 17/PhaIp from
*Pseudomonas putida* (Q5QBP4)
MAKVTVKKKDDALGTLGEVRGYARKIWLAGIGAYARVGQEGSDYFQEL

VKAGEGVEKRGKKRIDKELDAANNQIDEAAEEVSRVRGEVEIQLDKIE

KAFDARVGRALNRLGIPSKHDVEALSIKLEQLHELLERVAHKP

SEQ ID No 18/phaPlp from
*Rastonia eutropha* H16 (Q0KBV4)
MILTPEQVAAAQKANLETLFGLTTKAFEGVEKLVELNLQVVKTSFAEG

VDNAKKALSAKDAQELLAIQAAAVQPVAEKTLAYTRHLYEIASETQSE

FTKVAEAQLAEGSKNVQALVENLAKNAPAGSESTVAIVKSAISAANNA

YESVQKATKQAVEIAETNFQAAATAATKAAQQASATARTATAKKTTAA

Method for Producing Poly-Lactic Acid (PLA) Using Recombinant Yeast Cells

The invention further relates to a method for producing PLA by culturing recombinant yeast cells of the invention.

According to the invention, PLA may be produced by culturing such recombinant yeast cells in presence of lactic acid.

In a particular embodiment, the recombinant yeast cells are first cultivated in a fermentation broth devoid of lactic acid. For instance, such fermentation broth comprises low cost carbon source such as wheat bran or refined sugars such as glucose, galactose, xylose, saccharose, glycerol, etc., as a carbon source. Then, the fermentation broth is implemented with lactic acid to allow the production of PLA. This lactic acid can be produced by a microorganism such as lactic bacteria directly in the same fermentation broth. Alternatively, the lactic acid can be produced by a microorganism such as lactic bacteria in a different fermentation broth connected or not with the PLA production fermentation broth.

Advantageously, the fermentation broth comprises at least D-LA, in order to produce PDLA.

In a particular embodiment, a D-lactic acid dehydrogenase has been inactivated in the recombinant yeast cell, further containing a PDLA synthase, in order to favor the production of PDLA.

In a particular embodiment, the pH in the medium is controlled in order to increase the uptake of lactic acid from the medium into the cell. Preferably, the pH is maintained between 3 and 7, more preferably between 3 and 4.

Advantageously, the method of the invention leads to the production of at least 0.01 g of PLA/g dry cells, at least 0.02g, 0.03g, 0.04g, 0.05g, 0.1g, 0.2g, 0.5g, or more of PLA/g dry cells. Preferably, the method of the invention leads to the production of at least 1 g of PLA/g dry cells.

In a particular embodiment, the method of the invention comprises the step of recovering PLA of the cells and optionally the step of purifying the extracted PLA.

The PLA may be extracted from the yeast cells by any method known by the skilled person.

In a particular embodiment, the cells are lysed before recovering the PLA. Particularly, the cells may be lysed biologically, by contacting them with an enzyme able to digest their cell walls (e.g. zymolyase). Alternatively, the yeast cells may be lysed mechanically, by breaking their cell walls, for instance using a vortex with glass beads or lysed chemically, for instance by osmotic shock or alkali treatment.

The PLA may be extracted directly from non-lysed cells or after lysis using a solvent extraction process such as Soxhlet extraction (Yamada et al., 2011), maceration in solvent (i.e. chloroform, dichloromethane, acetone, etc.), filtration and precipitation, or ultracentrifugation, etc. After extraction and solubilization, PLA purification may be executed by using the precipitation method according to Matsumoto et al., (2005) or any other method known to the person skilled in the art.

According to the invention, the PLA recovered has advantageously a molecular weight (Mw) greater than 40,000 g/mol, 50,000 g/mol, 60,000 g/mol, 70,000 g/mol or 80,000 g/mol.

The invention further provides a fermentation broth comprising such recombinant yeast cells, and/or of a cell-free extract of such recombinant yeast cells, selected from cell supernatant, cell debris and cell walls extract. The invention further relates to dried recombinant yeast cells, containing PLA in their cytosol and/or peroxisome and/or mitochondria. According to the invention, such fermentation broth and/or dried cells may be used directly as raw material for producing plastic products or the like. For instance, dried cells of the invention may be directly introduced in an extruder, optionally with other polyesters, including other PLA, to provide PLA containing material and/or PLA containing plastic products.

Generally speaking, the present invention proposes to use recombinant yeast cells as described above, for producing PLA, preferably PDLA. The produced PLA interestingly exhibits a high molecular weight (Mw), generally greater than 40,000 g/mol, 50,000 g/mol, 60,000 g/mol, 70,000 g/mol or 80,000 g/mol.

It is therefore an object of the present invention to provide PLA, more particularly PDLA, having a molecular weight (Mw) greater than 40,000 g/mol, 50,000 g/mol, 60,000 g/mol, 70,000 g/mol or 80,000 g/mol.

Further aspects and advantages of the invention will be disclosed in the following examples, which should be considered as illustrative and do not limit the scope of this application.

EXAMPLES

Example 1: Construction of Yeast Strains Unable to Assimilate Lactic Acid

Construction of Disrupted Strains Followed by Marker Excision

The disruption cassettes were generated by PCR amplification on *Y. lipolytica* genomic DNA. It consists in a first amplification of a promoter region (P) and a termination region (T) of the gene to be deleted. The primers were designed as described by Fickers and coworkers (2003) and/or as described by Beopoulos et al. (2008 and 2011). After a secondary amplification consisting in a fusion of the P and T fragments, the resulting PT cassette was then inserted into the PCR4®Blunt-TOPO vector from Life Technologies (Carlsbad, Calif.). Then the auxotrophic marker URA3ex or LEU2ex was inserted into the PT vector through the IsceI specific cloning site to generate the corresponding plasmid (PUT or PLT, respectively). The PUT or PLT disruption cassette was introduced into *Y. lipolytica* by transformation with the lithium acetate method (Barth et al. 1996). Transformants were selected on the adequate minimal medium. Verification primers coding for specific sequences present in the auxotrophic marker and in the gene were used to verify gene disruption by PCR amplification of the genomic loci. Marker rescue was performed after transformation with the replicative plasmid pUB-CreI as described by Fickers and coworkers (2003).

Effect of Y1DLD1 Disruption on Growth on D-Lactate.

Growth of Y1DLD1 knockout strain (ThY1_434—MATA ura3-302 leu2-270 xpr2-322, ku70Δ, zeta, DLD1::URA3, LEU2ex-) (SEQ ID No12: Y1DLD1 gene) was compared to the growth of the host strain (JMY2341—MATA ura3-302 leu2-270 xpr2-322, KU70::URA3ex, zeta-LEU2ex-) on YNB medium (1.7 g/L YNB, 5 g/L $NH_4Cl$, 50 mM phosphate buffer, pH6.8) containing 400 mg/L leucine and different carbon sources: 10 g/L Glucose, or 10 g/L DL-lactate, or 10 g/L D-lactate or 10 g/L L-lactate (FIGS. 4A and 4B). Growth on D-, L- and DL-lactate reaches the same $OD_{600nm}$ in the host strain while growth of the knockout strain on D-lactate is totally abolished and growth on DL-lactate reaches half of the $OD_{600nm}$ of the growth on L-lactate, suggesting that D-lactate is not consumed by the knockout strain and its growth is due to L-lactate consumption.

The Y1DLD1 disrupted strain can then be modified according to the invention in order to produce PLA, more preferably PDLA.

Effect of Y1CYB21 Deletion on Growth on L-Lactate.

Growth of Y1CYB21 knockout strain (ThY1_436—MATA ura3-302 leu2-270 xpr2-322, ku70Δ, zeta, CYB21::LEU2ex, URA3ex-) (SEQ ID No13: Y1CYB21 gene) was compared to growth of the host strain (JMY2341) on YNB medium containing 10 g/L L-lactate (FIGS. 5A and 5B). While the JMY2341 grows on L-lactate, which is completely consumed after 72 hours, the disrupted strain did not consume L-lactate and so, did not grow.

The Y1CYB21 knockout strain can then be modified according to the invention in order to produce PLA, more preferably PLLA.

Example 2: Construction of Yeast Strains Capable of Producing PLA

Cloning and Expression of Genes Under the Control of the TEF Constitutive Promoter Genes were amplified by PCR and placed under the control of the yeast TEF constitutive promoter (pTEF). Coding gene sequences were then inserted between the BamHI-AvrII sites of the JMP62-pTEF expression vector, containing the URA3ex or LEU2ex selective marker. Plasmids were then digested with NotI restriction enzyme and the released coding gene containing fragment was used to transform the strains by the lithium acetate method (Barth et al. 1996). Transformants were selected by their respective auxotrophy on the adequate minimal medium. Marker rescue was performed after transformation with the replicative plasmid pUB-CreI as described by Fickers and coworkers (2003).

Yeast Strain

*Y. lipolytica* strain used was derived from the strain JMY2159 described in Beopoulos et al., 2014 (QPF). The Y1DLD1 gene (SEQ ID No12) was deleted to produce the strain ThY1_967 using the protocol described in Example 1 and FIG. 6. A variant of Pctp from *C. propionicum* (SEQ ID No1) with mutation V193A (CpPctp opt V193A—gene: SEQ ID No14) and a variant of PHA synthase (PhaC1p opt E130D S325T S477R Q481M—SEQ ID No11) from *P. aeruginosa* PAO1 with mutations E130D; S325T; S477R; Q481M (gene: SEQ ID No15) were expressed under the control of the same TEF promoter. The variant of the Pctp was expressed in the cytosol and the variant of the PhaC1p was targeted to the peroxisomes. Finally, the genotype of the ThY1_976 strain used in this example was: MATA ura3-302 leu2-270 xpr2-322, pox1-6Δ, dga1Δ, lro1Δ, dga2Δ, fad2Δ, dld1Δ, pTEF-PaPHAC1 opt E130D, S325T, S477R, Q481M, perox-URA3ex, pTEF-CpPCT opt V193A cyto-LEU2ex as shown in FIG. 6.

Culture Conditions

The ThY1_976 recombinant yeast cells were first cultured on rich medium (10 g/L yeast extract, 10 g/L peptone, 10 g/L glucose) at 28° C. overnight. Cells were then harvested by centrifugation to remove medium and resuspended in controlled medium with L-lactic acid as the sole carbon source and D-lactic acid as synthon for PDLA production (1.7 g/L YNB, 2 g/L casamino acids, 5 g/L NH$_4$Cl, 20 g/L DL-lactic acid, 50 mM phosphate buffer) with an initial OD$_{600nm}$ around 10. L-lactic acid was added when needed. Alternatively, for enhanced polymer accumulation, cells were resuspended in controlled medium with glucose and L-lactic acid as carbon source and D-lactic acid as synthon for PDLA production (1.7 g/L YNB, 2 g/L casamino acids, 5 g/L NH$_4$Cl, 40 g/L glucose, 15 g/L L-lactic acid, 5 g/L D-lactic acid, 50 mM phosphate buffer) with an initial OD$_{600nm}$ around 0.5. The cultures were grown at 28° C., with an agitation of 100 rpm for 150 hours and at indicated time cells were then harvested by centrifugation, washed twice with water and the cell pellet was kept at −80° C. until further analysis. Culture media was filtered through a 0.4 μm filter and kept at −20° C. until analyzed (see FIG. 9).

Polymer Extraction

About 1.5g of lyophilized cells were resuspended in 15 mL 100 mM Tris, pH8, 0.5 mg/mL zymolyase and incubated at 25° C. overnight. Cell suspensions were frozen at −80° C. and/or freeze dried by lyophilization until polymer extraction.

Produced polymer was extracted using a Soxhlet apparatus and chloroform. About 1.5g of dried cells was used and the chamber of the Soxhlet apparatus was filled 10 times before solvent and extracted materials were collected.

Alternatively, after extraction PLA can be precipitated by adding hexane (or cyclohexane) to the mixture.

Analysis

Glucose concentration was determined using a YSI 2900 analyser (System C industrie, St Paul Trois Chateaux, France).

Lactic acid concentration was determined by high-performance liquid chromatography (HPLC) using Thermo Fisher Scientific system (Courtaboeuf, France) equipped with a UV detector at 254 nm and a Phenomenex column (Chirex 3126 (D)-penicillamine 150×4.6 mm, Le Pecq, France) using 2 mM CuSO$_4$, 15% methanol (v/v) as the mobile phase at 1 mL/min.

Polymer composition was determined by NMR on a Bruker Avance II 500 spectrometer. The cells extracts were thoroughly dried, prior to being diluted in CDCl$_3$ containing 1% TMS (internal standard) and transferred to 5 mm NMR tubes. NMR spectra were recorded at 298 K. Each NMR spectrum was acquired using an excitation flip angle of 30° at a radiofrequency field of 29.7 kHz, a relaxation delay of 10 seconds and 2 dummy scans. For each experiment, 16 scans were performed with a repetition delay of 6.5 seconds. PLA concentrations were determined by integration of the specific quadruplet signal at 4.19 ppm.

Weight average molecular weight (Mw) and dispersity of the polymer were determined by gel permeation chromatography (GPC) at 20° C. using a Shimadzu system (Marne la Vallée, France) equipped with Wyatt detectors (MALLS, Dawn Heleos-II, 18 angles and refractometer at 22° C., Optilab T-rEX, Toulouse, France) with two Agilent columns (PLGel 5 um MIXED-C 300×7.5 mm). The elution solvent used was dichloromethane. Samples were resuspended in dichloromethane and filtered through a 0.4 μm filter. The molecular weight Mw and dispersity were calculated using do/dc value previously determined and equal to 0.0296.

PLA Purification and Composition Analysis

After extraction, PLA was diluted in chloroform and purified by precipitation by adding 10 volumes of hexane (adapted from Yamada et al., 2011). The precipitant was then collected by filtration on PTFE membrane. Complete hydrolysis of the polymer was performed at 180° C. and 100 bars during 50 minutes, according to Faisal et al. (2007) in order to identify the isomer of lactic acid which composed the polymer.

Results

In a first time, cultures were carried out in DL lactate, using L-lactic acid as the sole carbon source. Yeast growth was measured at an OD of 600 nm and substrate concentrations were measured over time. After 120 hours of culture, cells were collected and treated as for to extract PLA. PLA synthesis was demonstrated using NMR, based on the PLA specific signals and quantified using an internal standard (TMS) (FIG. 7). The NMR data demonstrate that the ThY1_976 recombinant strain exhibiting both CoA-transferase activity and lactyl-CoA polymerase activity produces PLA, while the strain that does not exhibit the aforementioned activities (ThY1_964, see FIG. 6), does not (spectrum 1 vs 2 of FIG. 7). The spectrum also shows that the main contaminants of the Soxhlet extractions are fatty acids, primarily constituted of oleic acid, and are retrieved in both extracts in similar proportions. Spectrum 3 shows the specific signals obtained using commercial PLA. The analysis reveals that synthesized polymer is a homopolymer containing 100% of lactic acid monomer. PLA molecular weight Mw and dispersity were quantified using GPC. Produced PLA Mw reached 43,800 g/mol after 120 hours of culture with a dispersity of 1.4. When cultured in DL-lactate with L-lactic acid used as the sole carbon source, recombinant cells accumulate 1.9% (g/g) PLA over the duration of the culture with a final biomass concentration around 2.5 g/L.

To improve PLA accumulation and biomass production, other carbon sources were tested. Both can be greatly improved using glucose as an additional carbon source. When cultured with DL-lactate and glucose, with L-lactic acid and glucose as carbon source, substrates concentration were followed and added when needed. D-lactic acid concentration was also measured and it slowly decreased over time indicating that it is used for the production of a polymer of PLA (FIG. 8).

PLA production started during the exponential phase (first 48 hours) with a productivity of 0.21 mg/g/h. Productivity then increased to 0.33 mg/g/h during the stationary phase. After 150 hours of culture, the total biomass was around 10.5g dry cell weight per liter and the total PLA production reached 0.5 g/L. Accumulation of PLA was then 4.25% (g/g) (FIG. 9).

After extraction, PLA was precipitated and its complete hydrolysis was performed at 180° C., 100 bars for 50 minutes. PLA composition was then determined by HPLC analysis on chiral column. This analysis reveals that the PLA is composed with 100% of D-lactic acid (FIG. 10).

Example 3: Improvement of PLA Production by Adding Two Copies of Genes Pctp Opt V193A or PhaC1 Opt E130D S325T S477R Q481M Yeast Strain Construction

*Y. lipolytica* strain used was derived from the strain ThY1_976 described in Example 2 and expressing one copy of a variant of Pctp from *C. propionicum* (SEQ ID No1) with mutation V193A (CpPctp opt V193A) and one copy of a variant of PHA synthase (PhaC1p opt E130D S325T S477R Q481M) from *P. aeruginosa* PAO1 with mutations E130D; S325T; S477R; Q481M (SEQ ID No11). A second copy of the gene encoding for the variant of Pctp from *C. propionicum* (SEQ ID No1) with mutation V193A (CpPctp opt V193A) and/or a second copy of the variant of PHA synthase (PhaC1p opt E130D S325T S477R Q481M) from *P. aeruginosa* PAO1 with mutations E130D; S325T; S477R; Q481M (gene SEQ ID No15) were expressed in the strain ThY1_976 with the same targeting than the first copy (cytosol or peroxisome).

The different strains used in this example were built with one or two copies of Pctp gene and one or two copies of PhaC1p gene under the control of the TEF promoter. The genotypes of the strains of this example are described in Table 3.

TABLE 3

Name and genotype of strains with one or two copies of genes of interest

| Strain | Number of copies of CpPctp opt V193A (targeted to cytosol) | Number of copies of PhaC1p opt E130D S325T S477R Q481M (targeted to peroxisome) | Genotype |
|---|---|---|---|
| ThYl_976 | 1 | 1 | QPF, Δdld1, pTEF-PaPHAC opt E130D, S325T, S477R, Q481M, perox-URA3ex, pTEF-CpPCT opt V193A, cyto-LEU2ex |
| ThYl_1086 | 2 | 2 | QPF, Δdld1, pTEF-PaPHAC opt E130D, S325T, S477R, Q481M, perox, pTEF-CpPCT opt V193A, cyto, pTEF-PaPHAC opt E130D, S325T, S477R, Q481M, perox-URA3ex, pTEF-CpPCT opt V193A, cyto-LEU2ex |

Culture Condition, Polymer Extraction and Analysis

The recombinant yeast cells were first cultured on rich medium (10 g/L yeast extract, 10 g/L peptone, 10 g/L glucose) at 28° C. overnight. Cells were then resuspended in controlled medium with glucose and L-lactic acid as carbon source and D-lactic acid as synthon for PDLA production (1.7 g/L YNB, 2 g/L casamino acids, 5 g/L $NH_4Cl$, 40 g/L glucose, 10 g/L DL-lactic acid, 50 mM phosphate buffer) with an initial $OD_{600nm}$ around 0.5. The cultures were grown at 28° C., with an agitation of 100 rpm for 5 days, and cells were then harvested by centrifugation, washed twice with water and the cell pellet was kept at −80° C. until further analysis. Culture media was filtered through a 0.4 μm filter and kept at −20° C. until analyzed.

Polymer extraction and NMR analysis were done as described in example 2.

Results

After 5 days of culture, cells were collected and PLA extracted. PLA accumulation (determined by quantitative NMR) in ThY1_1086 was improved by about 42% when two copies of both genes were introduced into the genome compared to the control strain ThY1_976.

Example 4: Improvement of PLA Production by Using a Strong and Constitutive Promoter (4UAS-TEF)

Cloning and Expression of Genes Under the Control of the 4UAS-TEF Strong and Constitutive Promoter and Yeast Strain Construction Genes were amplified by PCR and placed under the control of the yeast strong and constitutive 4UAS-TEF promoter. The cloning and expression were performed using the same technic described in Example 2.

*Y. lipolytica* strain used was derived from the strain ThY1_967 described in Example 2. A variant of Pctp from *C. propionicum* (SEQ ID No1) with mutation V193A (CpPctp opt V193A) was expressed in the cytosol and a variant of PHA synthase (PhaC1p opt E130D S325T S477R Q481M—SEQ ID No11) from *P. aeruginosa* PAO1 with mutations E130D; S325T; S477R; Q481M (gene SEQ ID No15) was expressed in the peroxisome. For both genes, promoter TEF and 4UAS-TEF were used. The different strains used in this example were built with one or two gene under the control of the TEF promoter or the 4UAS-TEF promoter. The genotypes of the strain used in this example were described in the table 4.

TABLE 4

Name and genotype of strains with genes under the control of different promoters

| Strain | Promoter used for CpPctp opt V193A | Promoter used for PhaC1p opt E130D S325T S477R Q481M | Genotype |
|---|---|---|---|
| ThYl_976 (control strain) | pTEF | pTEF | QPF, Δdld1, pTEF-PaPHAC opt E130D, S325T, S477R, Q481M, perox-URA3ex, pTEF-CpPCT opt V193A, cyto-LEU2ex |
| ThYl_1174 | p4UAS-TEF | pTEF | QPF, Δdld1, pTEF-PaPHAC opt E130D, S325T, S477R, Q481M, perox-URA3ex, p4UAS-TEF-CpPCT opt V193A, cyto-LEU2ex |
| ThYl_1156 | p4UAS-TEF | p4UAS-TEF | QPF, Δdld1, p4UAS-TEF-PaPHAC opt E130D, S325T, S477R, Q481M, perox-URA3ex, p4UAS-TEF-CpPCT opt V193A, cyto-LEU2ex |

Culture Condition, Polymer Extraction and Analysis

Culture conditions were the same as described in Example 3. Polymer extraction and analysis were the same as described in Example 2.

Results

After 5 days of culture, cells were collected and PLA extracted. Quantitative NMR results were described in the table 5. PLA accumulation was improved by about 28% when Pct gene was under the control of the strong promoter 4UAS-TEF and the PhaC1 gene under the control of the TEF promoter (Table 5, ThY1_1174 vs ThY1_976). Furthermore, PLA accumulation was even more increased, by about 46% when both genes were under the control of the strong promoter 4UAS-TEF (Table 5, ThY1_1156 vs ThY1_976).

TABLE 5

Accumulation of PLA determined by quantitative NMR

| Strain | PLA accumulation (g/g) |
|---|---|
| ThYl_976 (control strain) | 2.4% |
| ThYl_1174 | 3.1% (+28.5% vs control strain) |
| ThYl_1156 | 3.5% (+46.2% vs control strain) |

REFERENCES

Barth G, Gaillardin C (1996) *Yarrowia lipolytica*. In: Wolf K (ed) Non conventional yeasts in biotechnology, vol 1. Springer-Verlag, Berlin, Heidelberg, N.Y., pp 313-388

Beopoulos A, Mrozova Z, Thevenieau F, Le Dall M T, Hapala I, Papanikolaou S, Chardot T, Nicaud J M (2008) Control of lipid accumulation in the yeast *Yarrowia lipolytica*. Appl Environ Microbiol 74 (24):7779-7789

Beopoulos A, Nicaud J M, Gaillardin C (2011) An overview of lipid metabolism in yeasts and its impact on biotechnological processes. Appl Microbiol Biotechnol 90 (4): 1193-1206

Beopoulous A., Verbeke J., Bordes F., Guicherd M., Bressy M., Marty A. and Nicaud J.-M. (2014) Metabolic engineering for ricinoleic acid production in the yeast *Yarrowia lipolitica*. Appl. Microbiol. Biotechnol. 98(1):25-262

Faisal M., Saeki T., Tsuji T., Daimon H. and Fujie K. (2007) Depolymerization of poly(L-lactic acid) under hydrothermal conditions. Asian J. of Chem. 19:1714-1722Fickers P, Le Dall M T, Gaillardin C, Thonart P, Nicaud J M (2003) New disruption cassettes for rapid gene disruption and marker rescue in the yeast *Yarrowia lipolytica*. J Microbiol Methods 55 (3):727-737

Matsumoto K, Takase K, Aoki E, Doi Y and Taguchi S (2005) Synergistic Effects of Glu130Asp Substitution in the Type II Poly-hydroxyalkanoate (PHA) Synthase: Enhancement of PHA Production and Alteration of Polymer Molecular Weight. Biomacromolecules 2005, 6, 99-104

Meile, L., Rohr, L. M., Geissmann, T. A., Herensperger, M., and Teuber, M. (2001). Characterization of the D-Xylulose 5-Phosphate/D-Fructose 6-Phosphate Phosphoketolase Gene (xfp) from *Bifidobacterium lactis*. J. Bacteriol. 183:2929-2936

Yamada M, Matsumoto K, Uramoto S, Motohashi R, Abe H and Taguchi S (2011) Lactate fraction dependent mechanical properties of semitransparent poly(lactate-co-3-hydroxybutyrate)s produced by control of lactyl-CoA monomer fluxes in recombinant *Escherichia coli*. Journal of Biotechnology 154:255-260

The invention claimed is:

1. A recombinant yeast cell suitable for producing polylactic acid (PLA), said recombinant cell comprising and expressing
   a gene encoding a lactyl-CoA synthase wherein the lactyl-CoA synthase is selected from the group consisting of a CoA transferase, a propionyl-CoA transferase (Pctp) and a CoA ligase, and
   a gene encoding a polyhydroxyalkanoate (PHA) synthase (PhaCp), wherein the recombinant yeast cell has been engineered for expressing the lactyl-CoA synthase in the cytosol and for expressing the PHA synthase in the peroxisome of said recombinant yeast cell.

2. The recombinant yeast cell of claim 1, comprising at least one nucleic acid sequence encoding a Pctp comprising the amino acid sequence set forth in SEQ ID NO: 1, SEQ ID NO:2, SEQ ID NO:3, SEQ ID NO:4, SEQ ID NO: 16 or a variant thereof having lactyl-CoA synthase activity.

3. The recombinant yeast cell of claim 1, comprising at least one nucleic acid sequence encoding a PHA synthase comprising the amino acid sequence set forth in SEQ ID NO:5, SEQ ID NO:6, SEQ ID NO:7 or SEQ ID NO:11 or a variant thereof having lactyl-CoA polymerase activity.

4. The recombinant yeast cell of claim 1, wherein at least one lactic acid oxidoreductase is inactivated.

5. The recombinant yeast cell of claim 4, wherein a gene encoding a lactic acid dehydrogenase is inactivated.

6. The recombinant yeast cell of claim 5, wherein a gene encoding a D-lactic acid dehydrogenase is inactivated.

7. The recombinant yeast cell of claim 1, wherein the TAG synthesis pathway is inactivated.

8. The recombinant yeast cell of claim 7, wherein at least one gene encoding for an endogenous diacylglycerol-transferase is inactivated.

9. The recombinant yeast cell of claim 1, wherein at least one citrate synthase is inactivated.

10. The recombinant yeast cell of claim 9, wherein at least one gene encoding for a citrate synthase is inactivated.

11. The recombinant yeast cell of claim 1, which is of the genus selected from the group consisting of *Yarrowia, Saccharomyces, Kluyveromyces, Candida, Pichia, Schizosaccharomyces, Zygosaccharomyces, Hansenula, Tricho-*

*sporon, Yamadazyma, Cryptococcus, Lipomyces, Rhodosporidium, Rhodotorula, Geotrichum, Kloeckera, Schwanniomyces, Brettanomyces, Debaryomyces* and *Issatchenkia*.

12. The recombinant yeast cell of claim 11, which is selected from the group consisting of *Yarrowia bubula, Yarrowia deformans, Yarrowia lipolytica, Yarrowia yakushimensis, Yarrowia galli, Yarrowia oslonensis, Yarrowia hollandica, Yarrowia phangngensis, Yarrowia alimentaria* and *Yarrowia porcina*.

13. The recombinant yeast cell of claim 12, wherein the yeast cell is a *Y. lipolytica* cell that has been engineered to express
at least one Pctp comprising the amino acid sequence set forth in SEQ ID NO: 1, SEQ ID NO:2, SEQ ID NO:3, SEQ ID NO:4, SEQ ID NO: 16, or a variant thereof having a lactyl-CoA synthase activity, in the cytosol of said cell,
at least one PhaCp comprising the amino acid sequence set forth in SEQ ID NO:5, SEQ ID NO:6, SEQ ID NO:7 or SEQ ID NO:11, or a variant thereof having a lactyl-CoA polymerase activity, and further comprising at its C-terminus the amino acid sequence set forth in SEQ ID NO:8 or at its N-terminus the amino acid sequence set forth in SEQ ID NO:9 in order to be addressed in the peroxisome, and wherein said recombinant yeast cell has been further engineered in order to inactivate at least one lactate oxidoreductase selected from YALI0E03212p and YALI0D12661p.

14. The recombinant yeast cell of claim 13, that has been further engineered to inactivate at least one acyl-CoA oxidases selected from YALI0E32835g, YALI0F10857g, YALI0D24750g, YALI0E27654g, YALI0C23859g and YALI0E06567g.

15. A method for preparing poly-lactic acid (PLA) comprising:
culturing recombinant yeast cells according to claim 1 in presence of lactic acid to produce PLA.

16. The method of claim 15, further comprising a step of recovering PLA produced.

17. The method of claim 15, wherein the PLA produced is a homo-PLA.

18. The method of claim 17, wherein the PLA produced is poly-D-lactic acid (PDLA).

19. A fermentation broth comprising recombinant yeast cells of claim 1.

20. The recombinant yeast cell of claim 1, wherein the PHA synthase comprises SEQ ID NO:5, SEQ ID NO:6, SEQ ID NO:7 or SEQ ID NO:11 and the lactyl-CoA synthase comprises SEQ ID NO:1, SEQ ID NO:2, SEQ ID NO:3, SEQ ID NO:4, or SEQ ID NO:16.

* * * * *

UNITED STATES PATENT AND TRADEMARK OFFICE
CERTIFICATE OF CORRECTION

PATENT NO. : 10,717,996 B2
APPLICATION NO. : 16/064494
DATED : July 21, 2020
INVENTOR(S) : Simon Dusseaux et al.

Page 1 of 1

It is certified that error appears in the above-identified patent and that said Letters Patent is hereby corrected as shown below:

In the Specification

Column 6,
Line 7, "isoleucine (Be);" should read --isoleucine (Ile);--.

In the Claims

Column 63,
Line 5, Claim 12 "claim 11" should read --claim 1--.

Signed and Sealed this
Seventeenth Day of November, 2020

Andrei Iancu
*Director of the United States Patent and Trademark Office*

SEQUENCE LISTING

<160> NUMBER OF SEQ ID NOS: 18

<210> SEQ ID NO 1
<211> LENGTH: 524
<212> TYPE: PRT
<213> ORGANISM: Clostridium propionicum

<400> SEQUENCE: 1

Met Arg Lys Val Pro Ile Ile Thr Ala Asp Glu Ala Ala Lys Leu Ile
1               5                   10                  15

Lys Asp Gly Asp Thr Val Thr Thr Ser Gly Phe Val Gly Asn Ala Ile
            20                  25                  30

Pro Glu Ala Leu Asp Arg Ala Val Glu Lys Arg Phe Leu Glu Thr Gly
        35                  40                  45

Glu Pro Lys Asn Ile Thr Tyr Val Tyr Cys Gly Ser Gln Gly Asn Arg
    50                  55                  60

Asp Gly Arg Gly Ala Glu His Phe Ala His Glu Gly Leu Leu Lys Arg
65                  70                  75                  80

Tyr Ile Ala Gly His Trp Ala Thr Val Pro Ala Leu Gly Lys Met Ala
                85                  90                  95

Met Glu Asn Lys Met Glu Ala Tyr Asn Val Ser Gln Gly Ala Leu Cys
            100                 105                 110

His Leu Phe Arg Asp Ile Ala Ser His Lys Pro Gly Val Phe Thr Lys
        115                 120                 125

Val Gly Ile Gly Thr Phe Ile Asp Pro Arg Asn Gly Gly Gly Lys Val
    130                 135                 140

Asn Asp Ile Thr Lys Glu Asp Ile Val Glu Leu Val Glu Ile Lys Gly
145                 150                 155                 160

Gln Glu Tyr Leu Phe Tyr Pro Ala Phe Pro Ile His Val Ala Leu Ile
                165                 170                 175

Arg Gly Thr Tyr Ala Asp Glu Ser Gly Asn Ile Thr Phe Glu Lys Glu
            180                 185                 190

Val Ala Pro Leu Glu Gly Thr Ser Val Cys Gln Ala Val Lys Asn Ser
        195                 200                 205

Gly Gly Ile Val Val Val Gln Val Glu Arg Val Val Lys Ala Gly Thr
    210                 215                 220

Leu Asp Pro Arg His Val Lys Val Pro Gly Ile Tyr Val Asp Tyr Val
225                 230                 235                 240

Val Val Ala Asp Pro Glu Asp His Gln Gln Ser Leu Asp Cys Glu Tyr
                245                 250                 255

Asp Pro Ala Leu Ser Gly Glu His Arg Arg Pro Glu Val Val Gly Glu
            260                 265                 270

Pro Leu Pro Leu Ser Ala Lys Lys Val Ile Gly Arg Arg Gly Ala Ile
        275                 280                 285

Glu Leu Glu Lys Asp Val Ala Val Asn Leu Gly Val Gly Ala Pro Glu
    290                 295                 300

Tyr Val Ala Ser Val Ala Asp Glu Glu Gly Ile Val Asp Phe Met Thr
305                 310                 315                 320

Leu Thr Ala Glu Ser Gly Ala Ile Gly Gly Val Pro Ala Gly Gly Val
                325                 330                 335

Arg Phe Gly Ala Ser Tyr Asn Ala Asp Ala Leu Ile Asp Gln Gly Tyr
            340                 345                 350

Gln Phe Asp Tyr Tyr Asp Gly Gly Gly Leu Asp Leu Cys Tyr Leu Gly
        355                 360                 365

-continued

```
Leu Ala Glu Cys Asp Glu Lys Gly Asn Ile Asn Val Ser Arg Phe Gly
    370                 375                 380

Pro Arg Ile Ala Gly Cys Gly Phe Ile Asn Ile Thr Gln Asn Thr
385                 390                 395                 400

Pro Lys Val Phe Phe Cys Gly Thr Phe Thr Ala Gly Gly Leu Lys Val
                405                 410                 415

Lys Ile Glu Asp Gly Lys Val Ile Ile Val Gln Glu Gly Lys Gln Lys
                420                 425                 430

Lys Phe Leu Lys Ala Val Glu Gln Ile Thr Phe Asn Gly Asp Val Ala
            435                 440                 445

Leu Ala Asn Lys Gln Gln Val Thr Tyr Ile Thr Glu Arg Cys Val Phe
450                 455                 460

Leu Leu Lys Glu Asp Gly Leu His Leu Ser Glu Ile Ala Pro Gly Ile
465                 470                 475                 480

Asp Leu Gln Thr Gln Ile Leu Asp Val Met Asp Phe Ala Pro Ile Ile
                485                 490                 495

Asp Arg Asp Ala Asn Gly Gln Ile Lys Leu Met Asp Ala Ala Leu Phe
                500                 505                 510

Ala Glu Gly Leu Met Gly Leu Lys Glu Met Lys Ser
            515                 520

<210> SEQ ID NO 2
<211> LENGTH: 694
<212> TYPE: PRT
<213> ORGANISM: Aspergillus nidulans

<400> SEQUENCE: 2

Met Thr His Pro Gln Gln Ala Val His Ala Ala Ser Leu Gln Asn Pro
1               5                   10                  15

Glu Ala Phe Trp Ser His His Ala Gln Gln Leu His Trp His Lys Lys
                20                  25                  30

Pro Ser Arg Ala Ile Gly Arg Ser Thr Lys Thr Leu Ala Ser Gly Ala
            35                  40                  45

Ser His Glu Ser Trp Ser Trp Phe Pro Asp Gly Glu Ile Ser Thr Thr
        50                  55                  60

Tyr Asn Cys Val Asp Arg His Val Leu Asn Gly Asn Gly Asp Asn Val
65                  70                  75                  80

Ala Ile Ile Trp Asp Ser Ala Val Thr Gly Lys Lys Glu Lys Tyr Thr
                85                  90                  95

Tyr Arg Gln Leu Leu Asp Glu Val Glu Val Leu Ala Gly Val Leu Arg
            100                 105                 110

Glu Glu Gly Val Lys Lys Gly Asp Val Val Ile Ile Tyr Met Pro Met
        115                 120                 125

Ile Pro Ala Ala Leu Ile Gly Ala Leu Ala Val Ala Arg Leu Gly Ala
    130                 135                 140

Ile His Ala Ala Val Phe Gly Gly Phe Ala Ala Lys Ser Leu Ala Gln
145                 150                 155                 160

Arg Ile Glu Ala Ala Arg Pro Arg Ala Ile Leu Thr Ala Ser Cys Gly
                165                 170                 175

Ile Glu Gly Ala Lys Gly Pro Ile Ala Tyr Arg Pro Leu Val Glu Gly
            180                 185                 190

Ala Ile Glu Ala Ser Ser Phe Lys Pro Glu Lys Val Leu Ile Trp Gln
        195                 200                 205

Arg Asp Gln Leu Arg Trp Asn Asn Pro Asp Lys Leu Gly Gly Gln Arg
    210                 215                 220
```

-continued

```
Asn Trp Asn Arg Leu Val Lys Ser Ala Arg Met Arg Gly Ile Arg Ala
225                 230                 235                 240

Glu Pro Val Pro Val Arg Ser Thr Asp Gly Leu Tyr Ile Ile Tyr Thr
            245                 250                 255

Ser Gly Thr Thr Gly Leu Pro Lys Gly Val Val Arg Glu Ala Gly Gly
        260                 265                 270

His Ala Val Gly Leu Ser Leu Ser Ile Lys Tyr Leu Phe Asp Ile His
            275                 280                 285

Gly Pro Gly Asp Thr Met Phe Cys Ala Ser Asp Ile Gly Trp Val Val
    290                 295                 300

Gly His Ser Tyr Ile Leu Tyr Ala Pro Leu Leu Val Gly Ala Thr Thr
305                 310                 315                 320

Val Leu Phe Glu Gly Lys Pro Val Gly Thr Pro Asp Ala Gly Thr Phe
                325                 330                 335

Trp Arg Val Val Ala Glu His Lys Ala Asn Val Leu Phe Thr Ala Pro
            340                 345                 350

Thr Ala Leu Arg Ala Ile Arg Lys Glu Asp Pro Asp Asn Lys His Phe
        355                 360                 365

Glu Lys Val Ala Gly Asp Asn Asn Leu Arg His Leu Arg Ala Leu Phe
    370                 375                 380

Leu Ala Gly Glu Arg Ser Glu Pro Ser Ile Val Arg Ala Tyr Gln Asp
385                 390                 395                 400

Leu Leu Thr Lys His Ala Ala Arg Gly Ala Leu Val Val Asp Asn Trp
                405                 410                 415

Trp Ser Ser Glu Ser Gly Ser Pro Ile Ser Gly Leu Ala Leu Arg Ser
            420                 425                 430

Ala Val Gly Arg Val Pro Pro Arg Ser Asp Glu Tyr Asp Val Ala Pro
        435                 440                 445

Leu Ala Ile Arg Pro Gly Ser Ala Gly Leu Pro Met Pro Gly Phe Asp
    450                 455                 460

Val Arg Val Val Asp Asp Glu Gly Asn Glu Val Ala Gln Gly Thr Met
465                 470                 475                 480

Gly Asn Ile Val Met Ala Thr Pro Leu Ala Pro Thr Ala Phe Thr Arg
                485                 490                 495

Leu Phe Asn Asp Asp Glu Arg Phe Tyr Lys Gly Tyr Leu Lys Arg Phe
            500                 505                 510

Gly Gly Arg Trp Leu Asp Thr Gly Asp Ala Gly Met Ile Asp Gln Asp
        515                 520                 525

Gly Tyr Ile His Val Met Ser Arg Ser Asp Asp Ile Ile Asn Val Ala
    530                 535                 540

Ala His Arg Phe Ser Thr Gly Gln Gly Ser Ile Glu Gln Ala Ile Leu
545                 550                 555                 560

Ser His Pro Ala Ile Gly Glu Ala Ser Val Val Gly Ile Pro Asp Ala
                565                 570                 575

Leu Lys Gly His Leu Pro Phe Ala Phe Ile Thr Leu Lys Gln Ser Gly
            580                 585                 590

Gly Asn Ser Pro Ala Arg Pro Ser Ala Glu Leu Phe Asn Ser Val Asn
        595                 600                 605

Arg Leu Val Arg Glu Gln Ile Gly Ala Ile Ala Ser Leu Gly Gly Met
    610                 615                 620

Ile Gln Gly Gln Gly Met Ile Pro Lys Thr Arg Ser Gly Lys Thr Leu
625                 630                 635                 640
```

-continued

Arg Arg Val Leu Arg Glu Leu Val Glu Asn Gly Ala Arg Gly Glu Phe
            645                 650                 655

Glu Lys Glu Val Ala Val Pro Pro Thr Val Glu Asp Arg Gly Val Val
        660                 665                 670

Glu Val Ala Arg Glu Lys Val Arg Glu Tyr Phe Glu Ser Gln Ser Gly
        675                 680                 685

Ser Pro Lys Ala Lys Leu
        690

<210> SEQ ID NO 3
<211> LENGTH: 531
<212> TYPE: PRT
<213> ORGANISM: Escherichia coli

<400> SEQUENCE: 3

Met Lys Pro Val Lys Pro Arg Ile Asn Gly Arg Val Pro Val Leu
1               5                   10                  15

Ser Ala Gln Glu Ala Val Asn Tyr Ile Pro Asp Glu Ala Thr Leu Cys
            20                  25                  30

Val Leu Gly Ala Gly Gly Gly Ile Leu Glu Ala Thr Thr Leu Ile Thr
        35                  40                  45

Ala Leu Ala Asp Lys Tyr Lys Gln Thr Gln Thr Pro Arg Asn Leu Ser
    50                  55                  60

Ile Ile Ser Pro Thr Gly Leu Gly Asp Arg Ala Asp Arg Gly Ile Ser
65                  70                  75                  80

Pro Leu Ala Gln Glu Gly Leu Val Lys Trp Ala Leu Cys Gly His Trp
                85                  90                  95

Gly Gln Ser Pro Arg Ile Ser Asp Leu Ala Glu Gln Asn Lys Ile Ile
            100                 105                 110

Ala Tyr Asn Tyr Pro Gln Gly Val Leu Thr Gln Thr Leu Arg Ala Ala
        115                 120                 125

Ala Ala His Gln Pro Gly Ile Ile Ser Asp Ile Gly Ile Gly Thr Phe
    130                 135                 140

Val Asp Pro Arg Gln Gln Gly Gly Lys Leu Asn Glu Val Thr Lys Glu
145                 150                 155                 160

Asp Leu Ile Lys Leu Val Glu Phe Asp Asn Lys Glu Tyr Leu Tyr Tyr
                165                 170                 175

Lys Ala Ile Ala Pro Asp Ile Ala Phe Ile Arg Ala Thr Thr Cys Asp
            180                 185                 190

Ser Glu Gly Tyr Ala Thr Phe Glu Asp Glu Val Met Tyr Leu Asp Ala
        195                 200                 205

Leu Val Ile Ala Gln Ala Val His Asn Asn Gly Gly Ile Val Met Met
    210                 215                 220

Gln Val Gln Lys Met Val Lys Lys Ala Thr Leu His Pro Lys Ser Val
225                 230                 235                 240

Arg Ile Pro Gly Tyr Leu Val Asp Ile Val Val Asp Pro Asp Gln
                245                 250                 255

Ser Gln Leu Tyr Gly Gly Ala Pro Val Asn Arg Phe Ile Ser Gly Asp
            260                 265                 270

Phe Thr Leu Asp Asp Ser Thr Lys Leu Ser Leu Pro Leu Asn Gln Arg
        275                 280                 285

Lys Leu Val Ala Arg Arg Ala Leu Phe Glu Met Arg Lys Gly Ala Val
    290                 295                 300

Gly Asn Val Gly Val Gly Ile Ala Asp Gly Ile Gly Leu Val Ala Arg
305                 310                 315                 320

Glu Glu Gly Cys Ala Asp Asp Phe Ile Leu Thr Val Glu Thr Gly Pro
            325                 330                 335

Ile Gly Gly Ile Thr Ser Gln Gly Ile Ala Phe Gly Ala Asn Val Asn
            340                 345                 350

Thr Arg Ala Ile Leu Asp Met Thr Ser Gln Phe Asp Phe Tyr His Gly
            355                 360                 365

Gly Gly Leu Asp Val Cys Tyr Leu Ser Phe Ala Glu Val Asp Gln His
        370                 375                 380

Gly Asn Val Gly Val His Lys Phe Asn Gly Lys Ile Met Gly Thr Gly
385                 390                 395                 400

Gly Phe Ile Asp Ile Ser Ala Thr Ser Lys Lys Ile Ile Phe Cys Gly
                405                 410                 415

Thr Leu Thr Ala Gly Ser Leu Lys Thr Glu Ile Ala Asp Gly Lys Leu
            420                 425                 430

Asn Ile Val Gln Glu Gly Arg Val Lys Lys Phe Ile Arg Glu Leu Pro
            435                 440                 445

Glu Ile Thr Phe Ser Gly Lys Ile Ala Leu Glu Arg Gly Leu Asp Val
        450                 455                 460

Arg Tyr Ile Thr Glu Arg Ala Val Phe Thr Leu Lys Glu Asp Gly Leu
465                 470                 475                 480

His Leu Ile Glu Ile Ala Pro Gly Val Asp Leu Gln Lys Asp Ile Leu
                485                 490                 495

Asp Lys Met Asp Phe Thr Pro Val Ile Ser Pro Glu Leu Lys Leu Met
            500                 505                 510

Asp Glu Arg Leu Phe Ile Asp Ala Ala Met Gly Phe Val Leu Pro Glu
            515                 520                 525

Ala Ala His
        530

<210> SEQ ID NO 4
<211> LENGTH: 542
<212> TYPE: PRT
<213> ORGANISM: Ralstonia. eutropha

<400> SEQUENCE: 4

Met Lys Val Ile Thr Ala Arg Glu Ala Ala Leu Val Gln Asp Gly
1               5                   10                  15

Trp Thr Val Ala Ser Ala Gly Phe Val Gly Ala Gly His Ala Glu Ala
            20                  25                  30

Val Thr Glu Ala Leu Glu Gln Arg Phe Leu Gln Ser Gly Leu Pro Arg
        35                  40                  45

Asp Leu Thr Leu Val Tyr Ser Ala Gly Gln Gly Asp Arg Gly Ala Arg
    50                  55                  60

Gly Val Asn His Phe Gly Asn Ala Gly Met Thr Ala Ser Ile Val Gly
65                  70                  75                  80

Gly His Trp Arg Ser Ala Thr Arg Leu Ala Thr Leu Ala Met Ala Glu
                85                  90                  95

Gln Cys Glu Gly Tyr Asn Leu Pro Gln Gly Val Leu Thr His Leu Tyr
            100                 105                 110

Arg Ala Ile Ala Gly Gly Lys Pro Gly Val Met Thr Lys Ile Gly Leu
        115                 120                 125

His Thr Phe Val Asp Pro Arg Thr Ala Gln Asp Ala Arg Tyr His Gly
    130                 135                 140

Gly Ala Val Asn Glu Arg Ala Arg Gln Ala Ile Ala Glu Gly Lys Ala

```
            145                 150                 155                 160
Cys Trp Val Asp Ala Val Asp Phe Arg Gly Asp Glu Tyr Leu Phe Tyr
                165                 170                 175

Pro Ser Phe Pro Ile His Cys Ala Leu Ile Arg Cys Thr Ala Ala Asp
                180                 185                 190

Ala Arg Gly Asn Leu Ser Thr His Arg Glu Ala Phe His His Glu Leu
                195                 200                 205

Leu Ala Met Ala Gln Ala Ala His Asn Ser Gly Gly Ile Val Ile Ala
            210                 215                 220

Gln Val Glu Ser Leu Val Asp His His Glu Ile Leu Gln Ala Ile His
225                 230                 235                 240

Val Pro Gly Ile Leu Val Asp Tyr Val Val Cys Asp Asn Pro Ala
                245                 250                 255

Asn His Gln Met Thr Phe Ala Glu Ser Tyr Asn Pro Ala Tyr Val Thr
                260                 265                 270

Pro Trp Gln Gly Glu Ala Ala Val Ala Glu Ala Glu Ala Ala Pro Val
                275                 280                 285

Ala Ala Gly Pro Leu Asp Ala Arg Thr Ile Val Gln Arg Arg Ala Val
            290                 295                 300

Met Glu Leu Ala Arg Arg Ala Pro Arg Val Val Asn Leu Gly Val Gly
305                 310                 315                 320

Met Pro Ala Ala Val Gly Met Leu Ala His Gln Ala Gly Leu Asp Gly
                325                 330                 335

Phe Thr Leu Thr Val Glu Ala Gly Pro Ile Gly Gly Thr Pro Ala Asp
                340                 345                 350

Gly Leu Ser Phe Gly Ala Ser Ala Tyr Pro Glu Ala Val Val Asp Gln
            355                 360                 365

Pro Ala Gln Phe Asp Phe Tyr Glu Gly Gly Ile Asp Leu Ala Ile
            370                 375                 380

Leu Gly Leu Ala Glu Leu Asp Gly His Gly Asn Val Asn Val Ser Lys
385                 390                 395                 400

Phe Gly Glu Gly Glu Gly Ala Ser Ile Ala Gly Val Gly Phe Ile
                405                 410                 415

Asn Ile Thr Gln Ser Ala Arg Ala Val Val Phe Met Gly Thr Leu Thr
                420                 425                 430

Ala Gly Gly Leu Glu Val Arg Ala Gly Asp Gly Leu Gln Ile Val
            435                 440                 445

Arg Glu Gly Arg Val Lys Lys Ile Val Pro Glu Val Ser His Leu Ser
450                 455                 460

Phe Asn Gly Pro Tyr Val Ala Ser Leu Gly Ile Pro Val Leu Tyr Ile
465                 470                 475                 480

Thr Glu Arg Ala Val Phe Glu Met Arg Ala Gly Ala Asp Gly Glu Ala
                485                 490                 495

Arg Leu Thr Leu Val Glu Ile Ala Pro Gly Val Asp Leu Gln Arg Asp
            500                 505                 510

Val Leu Asp Gln Cys Ser Thr Pro Ile Ala Val Ala Gln Asp Leu Arg
            515                 520                 525

Glu Met Asp Ala Arg Leu Phe Gln Ala Gly Pro Leu His Leu
            530                 535                 540

<210> SEQ ID NO 5
<211> LENGTH: 559
<212> TYPE: PRT
<213> ORGANISM: Pseudomonas aeruginosa PA01
```

<400> SEQUENCE: 5

```
Met Ser Gln Lys Asn Asn Asn Glu Leu Pro Lys Gln Ala Ala Glu Asn
1               5                   10                  15

Thr Leu Asn Leu Asn Pro Val Ile Gly Ile Arg Gly Lys Asp Leu Leu
            20                  25                  30

Thr Ser Ala Arg Met Val Leu Leu Gln Ala Val Arg Gln Pro Leu His
        35                  40                  45

Ser Ala Arg His Val Ala His Phe Ser Leu Glu Leu Lys Asn Val Leu
    50                  55                  60

Leu Gly Gln Ser Glu Leu Arg Pro Gly Asp Asp Arg Arg Phe Ser
65                  70                  75                  80

Asp Pro Ala Trp Ser Gln Asn Pro Leu Tyr Lys Arg Tyr Met Gln Thr
                85                  90                  95

Tyr Leu Ala Trp Arg Lys Glu Leu His Ser Trp Ile Ser His Ser Asp
            100                 105                 110

Leu Ser Pro Gln Asp Ile Ser Arg Gly Gln Phe Val Ile Asn Leu Leu
        115                 120                 125

Thr Glu Ala Met Ser Pro Thr Asn Ser Leu Ser Asn Pro Ala Ala Val
    130                 135                 140

Lys Arg Phe Phe Glu Thr Gly Gly Lys Ser Leu Leu Asp Gly Leu Gly
145                 150                 155                 160

His Leu Ala Lys Asp Leu Val Asn Asn Gly Met Pro Ser Gln Val
                165                 170                 175

Asp Met Asp Ala Phe Glu Val Gly Lys Asn Leu Ala Thr Thr Glu Gly
            180                 185                 190

Ala Val Val Phe Arg Asn Asp Val Leu Glu Leu Ile Gln Tyr Arg Pro
        195                 200                 205

Ile Thr Glu Ser Val His Glu Arg Pro Leu Leu Val Val Pro Pro Gln
    210                 215                 220

Ile Asn Lys Phe Tyr Val Phe Asp Leu Ser Pro Asp Lys Ser Leu Ala
225                 230                 235                 240

Arg Phe Cys Leu Arg Asn Gly Val Gln Thr Phe Ile Val Ser Trp Arg
                245                 250                 255

Asn Pro Thr Lys Ser Gln Arg Glu Trp Gly Leu Thr Thr Tyr Ile Glu
            260                 265                 270

Ala Leu Lys Glu Ala Ile Glu Val Val Leu Ser Ile Thr Gly Ser Lys
        275                 280                 285

Asp Leu Asn Leu Leu Gly Ala Cys Ser Gly Gly Ile Thr Thr Ala Thr
    290                 295                 300

Leu Val Gly His Tyr Val Ala Ser Gly Glu Lys Lys Val Asn Ala Phe
305                 310                 315                 320

Thr Gln Leu Val Ser Val Leu Asp Phe Glu Leu Asn Thr Gln Val Ala
                325                 330                 335

Leu Phe Ala Asp Glu Lys Thr Leu Glu Ala Ala Lys Arg Arg Ser Tyr
            340                 345                 350

Gln Ser Gly Val Leu Glu Gly Lys Asp Met Ala Lys Val Phe Ala Trp
        355                 360                 365

Met Arg Pro Asn Asp Leu Ile Trp Asn Tyr Trp Val Asn Asn Tyr Leu
    370                 375                 380

Leu Gly Asn Gln Pro Pro Ala Phe Asp Ile Leu Tyr Trp Asn Asn Asp
385                 390                 395                 400

Thr Thr Arg Leu Pro Ala Ala Leu His Gly Glu Phe Val Glu Leu Phe
```

```
                405                 410                 415
Lys Ser Asn Pro Leu Asn Arg Pro Gly Ala Leu Glu Val Ser Gly Thr
            420                 425                 430

Pro Ile Asp Leu Lys Gln Val Thr Cys Asp Phe Tyr Cys Val Ala Gly
            435                 440                 445

Leu Asn Asp His Ile Thr Pro Trp Glu Ser Cys Tyr Lys Ser Ala Arg
450                 455                 460

Leu Leu Gly Gly Lys Cys Glu Phe Ile Leu Ser Asn Ser Gly His Ile
465                 470                 475                 480

Gln Ser Ile Leu Asn Pro Pro Gly Asn Pro Lys Ala Arg Phe Met Thr
            485                 490                 495

Asn Pro Glu Leu Pro Ala Glu Pro Lys Ala Trp Leu Glu Gln Ala Gly
            500                 505                 510

Lys His Ala Asp Ser Trp Trp Leu His Trp Gln Gln Trp Leu Ala Glu
            515                 520                 525

Arg Ser Gly Lys Thr Arg Lys Ala Pro Ala Ser Leu Gly Asn Lys Thr
            530                 535                 540

Tyr Pro Ala Gly Glu Ala Ala Pro Gly Thr Tyr Val His Glu Arg
545                 550                 555

<210> SEQ ID NO 6
<211> LENGTH: 589
<212> TYPE: PRT
<213> ORGANISM: Ralstonia. eutropha H16

<400> SEQUENCE: 6

Met Ala Thr Gly Lys Gly Ala Ala Ser Thr Gln Glu Gly Lys Ser
1               5                   10                  15

Gln Pro Phe Lys Val Thr Pro Gly Pro Phe Asp Pro Ala Thr Trp Leu
            20                  25                  30

Glu Trp Ser Arg Gln Trp Gln Gly Thr Glu Gly Asn Gly His Ala Ala
            35                  40                  45

Ala Ser Gly Ile Pro Gly Leu Asp Ala Leu Ala Gly Val Lys Ile Ala
        50                  55                  60

Pro Ala Gln Leu Gly Asp Ile Gln Gln Arg Tyr Met Lys Asp Phe Ser
65                  70                  75                  80

Ala Leu Trp Gln Ala Met Ala Glu Gly Lys Ala Glu Ala Thr Gly Pro
                85                  90                  95

Leu His Asp Arg Arg Phe Ala Gly Asp Ala Trp Arg Thr Asn Leu Pro
            100                 105                 110

Tyr Arg Phe Ala Ala Ala Phe Tyr Leu Leu Asn Ala Arg Ala Leu Thr
            115                 120                 125

Glu Leu Ala Asp Ala Val Glu Ala Asp Ala Lys Thr Arg Gln Arg Ile
        130                 135                 140

Arg Phe Ala Ile Ser Gln Trp Val Asp Ala Met Ser Pro Ala Asn Phe
145                 150                 155                 160

Leu Ala Thr Asn Pro Glu Ala Gln Arg Leu Leu Ile Glu Ser Gly Gly
                165                 170                 175

Glu Ser Leu Arg Ala Gly Val Arg Asn Met Met Glu Asp Leu Thr Arg
            180                 185                 190

Gly Lys Ile Ser Gln Thr Asp Glu Ser Ala Phe Glu Val Gly Arg Asn
            195                 200                 205

Val Ala Val Thr Glu Gly Ala Val Val Phe Glu Asn Glu Tyr Phe Gln
        210                 215                 220
```

```
Leu Leu Gln Tyr Lys Pro Leu Thr Asp Lys Val His Ala Arg Pro Leu
225                 230                 235                 240

Leu Met Val Pro Pro Cys Ile Asn Lys Tyr Tyr Ile Leu Asp Leu Gln
            245                 250                 255

Pro Glu Ser Ser Leu Val Arg His Val Val Glu Gln Gly His Thr Val
        260                 265                 270

Phe Leu Val Ser Trp Arg Asn Pro Asp Ala Ser Met Ala Gly Ser Thr
    275                 280                 285

Trp Asp Asp Tyr Ile Glu His Ala Ala Ile Arg Ala Ile Glu Val Ala
    290                 295                 300

Arg Asp Ile Ser Gly Gln Asp Lys Ile Asn Val Leu Gly Phe Cys Val
305                 310                 315                 320

Gly Gly Thr Ile Val Ser Thr Ala Leu Ala Val Leu Ala Ala Arg Gly
                325                 330                 335

Glu His Pro Ala Ala Ser Val Thr Leu Leu Thr Leu Leu Asp Phe
            340                 345                 350

Ala Asp Thr Gly Ile Leu Asp Val Phe Val Asp Glu Gly His Val Gln
        355                 360                 365

Leu Arg Glu Ala Thr Leu Gly Gly Gly Ala Gly Ala Pro Cys Ala Leu
    370                 375                 380

Leu Arg Gly Leu Glu Leu Ala Asn Thr Phe Ser Phe Leu Arg Pro Asn
385                 390                 395                 400

Asp Leu Val Trp Asn Tyr Val Val Asp Asn Tyr Leu Lys Gly Asn Thr
                405                 410                 415

Pro Val Pro Phe Asp Leu Leu Phe Trp Asn Gly Asp Ala Thr Asn Leu
            420                 425                 430

Pro Gly Pro Trp Tyr Cys Trp Tyr Leu Arg His Thr Tyr Leu Gln Asn
        435                 440                 445

Glu Leu Lys Val Pro Gly Lys Leu Thr Val Cys Gly Val Pro Val Asp
    450                 455                 460

Leu Ala Ser Ile Asp Val Pro Thr Tyr Ile Tyr Gly Ser Arg Glu Asp
465                 470                 475                 480

His Ile Val Pro Trp Thr Ala Ala Tyr Ala Ser Thr Ala Leu Leu Ala
                485                 490                 495

Asn Lys Leu Arg Phe Val Leu Gly Ala Ser Gly His Ile Ala Gly Val
            500                 505                 510

Ile Asn Pro Pro Ala Lys Asn Lys Arg Ser His Trp Thr Asn Asp Ala
        515                 520                 525

Leu Pro Glu Ser Pro Gln Gln Trp Leu Ala Gly Ala Ile Glu His His
    530                 535                 540

Gly Ser Trp Trp Pro Asp Trp Thr Ala Trp Leu Ala Gly Gln Ala Gly
545                 550                 555                 560

Ala Lys Arg Ala Ala Pro Ala Asn Tyr Gly Asn Ala Arg Tyr Arg Ala
                565                 570                 575

Ile Glu Pro Ala Pro Gly Arg Tyr Val Lys Ala Lys Ala
            580                 585

<210> SEQ ID NO 7
<211> LENGTH: 355
<212> TYPE: PRT
<213> ORGANISM: Chromatium vinosum

<400> SEQUENCE: 7

Met Phe Pro Ile Asp Ile Arg Pro Asp Lys Leu Thr Gln Glu Met Leu
1               5                   10                  15
```

```
Asp Tyr Ser Arg Lys Leu Gly Gln Gly Met Glu Asn Leu Leu Asn Ala
            20                  25                  30

Glu Ala Ile Asp Thr Gly Val Ser Pro Lys Gln Ala Val Tyr Ser Glu
        35                  40                  45

Asp Lys Leu Val Leu Tyr Arg Tyr Asp Arg Pro Glu Gly Ala Pro Glu
    50                  55                  60

Ala Gln Pro Val Pro Leu Leu Ile Val Tyr Ala Leu Val Asn Arg Pro
65                  70                  75                  80

Tyr Met Thr Asp Ile Gln Glu Asp Arg Ser Thr Ile Lys Gly Leu Leu
                85                  90                  95

Ala Thr Gly Gln Asp Val Tyr Leu Ile Asp Trp Gly Tyr Pro Asp Gln
            100                 105                 110

Ala Asp Arg Ala Leu Thr Leu Asp Asp Tyr Ile Asn Gly Tyr Ile Asp
        115                 120                 125

Arg Cys Val Asp Tyr Leu Arg Glu Ala His Gly Val Asp Lys Val Asn
    130                 135                 140

Leu Leu Gly Ile Cys Gln Gly Gly Ala Phe Ser Leu Met Tyr Ser Ala
145                 150                 155                 160

Leu His Pro Asp Lys Val Arg Asn Leu Val Thr Met Val Thr Pro Val
                165                 170                 175

Asp Phe Lys Thr Pro Asp Asn Leu Leu Ser Ala Trp Val Gln Asn Val
            180                 185                 190

Asp Ile Asp Leu Ala Val Asp Thr Met Gly Asn Ile Pro Gly Glu Leu
        195                 200                 205

Leu Asn Trp Thr Phe Leu Ser Leu Lys Pro Phe Ser Leu Thr Gly Gln
    210                 215                 220

Lys Tyr Val Asn Met Val Asp Leu Leu Asp Pro Asp Lys Val Lys
225                 230                 235                 240

Asn Phe Leu Arg Met Glu Lys Trp Ile Phe Asp Ser Pro Asp Gln Ala
                245                 250                 255

Gly Glu Thr Phe Arg Gln Phe Ile Lys Asp Phe Tyr Gln Asn Asn Gly
            260                 265                 270

Phe Leu Asn Gly Val Val Leu Gly Gly Gln Glu Val Asp Leu Lys
        275                 280                 285

Asp Ile Thr Cys Pro Val Leu Asn Ile Phe Ala Leu Gln Asp His Leu
    290                 295                 300

Val Pro Pro Asp Ala Ser Arg Ala Leu Lys Gly Leu Thr Ser Ser Pro
305                 310                 315                 320

Asp Tyr Thr Glu Leu Ala Phe Pro Gly Gly His Ile Gly Ile Tyr Val
                325                 330                 335

Ser Gly Lys Ala Gln Lys Glu Val Thr Pro Ala Ile Gly Lys Trp Leu
            340                 345                 350

Asn Glu Arg
        355

<210> SEQ ID NO 8
<211> LENGTH: 14
<212> TYPE: PRT
<213> ORGANISM: artificial sequence
<220> FEATURE:
<223> OTHER INFORMATION: PTS1

<400> SEQUENCE: 8

Met Gly Ala Gly Val Thr Glu Asp Gln Phe Lys Ser Lys Leu
1               5                   10
```

<210> SEQ ID NO 9
<211> LENGTH: 16
<212> TYPE: PRT
<213> ORGANISM: artificial sequence
<220> FEATURE:
<223> OTHER INFORMATION: PTS2

<400> SEQUENCE: 9

Met Asp Arg Leu Asn Asn Leu Ala Thr Gln Leu Glu Gln Asn Pro Ala
1               5                   10                  15

<210> SEQ ID NO 10
<211> LENGTH: 26
<212> TYPE: PRT
<213> ORGANISM: artificial sequence
<220> FEATURE:
<223> OTHER INFORMATION: MTS

<400> SEQUENCE: 10

Met Leu Arg Leu Arg Thr Met Arg Pro Thr Gln Thr Ser Val Arg Ala
1               5                   10                  15

Ala Leu Gly Pro Thr Ala Ala Ala Arg Asn
            20                  25

<210> SEQ ID NO 11
<211> LENGTH: 559
<212> TYPE: PRT
<213> ORGANISM: artificial sequence
<220> FEATURE:
<223> OTHER INFORMATION: mutant of PhaCp from P. aeruginosa PA01

<400> SEQUENCE: 11

Met Ser Gln Lys Asn Asn Asn Glu Leu Pro Lys Gln Ala Ala Glu Asn
1               5                   10                  15

Thr Leu Asn Leu Asn Pro Val Ile Gly Ile Arg Gly Lys Asp Leu Leu
            20                  25                  30

Thr Ser Ala Arg Met Val Leu Gln Ala Val Arg Gln Pro Leu His
        35                  40                  45

Ser Ala Arg His Val Ala His Phe Ser Leu Glu Leu Lys Asn Val Leu
    50                  55                  60

Leu Gly Gln Ser Glu Leu Arg Pro Gly Asp Asp Arg Arg Phe Ser
65                  70                  75                  80

Asp Pro Ala Trp Ser Gln Asn Pro Leu Tyr Lys Arg Tyr Met Gln Thr
                85                  90                  95

Tyr Leu Ala Trp Arg Lys Glu Leu His Ser Trp Ile Ser His Ser Asp
            100                 105                 110

Leu Ser Pro Gln Asp Ile Ser Arg Gly Gln Phe Val Ile Asn Leu Leu
        115                 120                 125

Thr Asp Ala Met Ser Pro Thr Asn Ser Leu Ser Asn Pro Ala Ala Val
    130                 135                 140

Lys Arg Phe Phe Glu Thr Gly Gly Lys Ser Leu Leu Asp Gly Leu Gly
145                 150                 155                 160

His Leu Ala Lys Asp Leu Val Asn Asn Gly Gly Met Pro Ser Gln Val
                165                 170                 175

Asp Met Asp Ala Phe Glu Val Gly Lys Asn Leu Ala Thr Thr Glu Gly
            180                 185                 190

Ala Val Val Phe Arg Asn Asp Val Leu Glu Leu Ile Gln Tyr Arg Pro
        195                 200                 205

```
Ile Thr Glu Ser Val His Glu Arg Pro Leu Leu Val Val Pro Pro Gln
            210                 215                 220

Ile Asn Lys Phe Tyr Val Phe Asp Leu Ser Pro Asp Lys Ser Leu Ala
225                 230                 235                 240

Arg Phe Cys Leu Arg Asn Gly Val Gln Thr Phe Ile Val Ser Trp Arg
                245                 250                 255

Asn Pro Thr Lys Ser Gln Arg Glu Trp Gly Leu Thr Thr Tyr Ile Glu
            260                 265                 270

Ala Leu Lys Glu Ala Ile Glu Val Leu Ser Ile Thr Gly Ser Lys
                275                 280                 285

Asp Leu Asn Leu Leu Gly Ala Cys Ser Gly Gly Ile Thr Thr Ala Thr
            290                 295                 300

Leu Val Gly His Tyr Val Ala Ser Gly Glu Lys Lys Val Asn Ala Phe
305                 310                 315                 320

Thr Gln Leu Val Thr Val Leu Asp Phe Glu Leu Asn Thr Gln Val Ala
                325                 330                 335

Leu Phe Ala Asp Glu Lys Thr Leu Glu Ala Ala Lys Arg Arg Ser Tyr
            340                 345                 350

Gln Ser Gly Val Leu Glu Gly Lys Asp Met Ala Lys Val Phe Ala Trp
            355                 360                 365

Met Arg Pro Asn Asp Leu Ile Trp Asn Tyr Trp Val Asn Asn Tyr Leu
370                 375                 380

Leu Gly Asn Gln Pro Pro Ala Phe Asp Ile Leu Tyr Trp Asn Asn Asp
385                 390                 395                 400

Thr Thr Arg Leu Pro Ala Ala Leu His Gly Glu Phe Val Glu Leu Phe
                405                 410                 415

Lys Ser Asn Pro Leu Asn Arg Pro Gly Ala Leu Glu Val Ser Gly Thr
            420                 425                 430

Pro Ile Asp Leu Lys Gln Val Thr Cys Asp Phe Tyr Cys Val Ala Gly
            435                 440                 445

Leu Asn Asp His Ile Thr Pro Trp Glu Ser Cys Tyr Lys Ser Ala Arg
            450                 455                 460

Leu Leu Gly Gly Lys Cys Glu Phe Ile Leu Ser Asn Arg Gly His Ile
465                 470                 475                 480

Met Ser Ile Leu Asn Pro Gly Asn Pro Lys Ala Arg Phe Met Thr
                485                 490                 495

Asn Pro Glu Leu Pro Ala Glu Pro Lys Ala Trp Leu Glu Gln Ala Gly
            500                 505                 510

Lys His Ala Asp Ser Trp Trp Leu His Trp Gln Gln Trp Leu Ala Glu
            515                 520                 525

Arg Ser Gly Lys Thr Arg Lys Ala Pro Ala Ser Leu Gly Asn Lys Thr
530                 535                 540

Tyr Pro Ala Gly Glu Ala Ala Pro Gly Thr Tyr Val His Glu Arg
545                 550                 555

<210> SEQ ID NO 12
<211> LENGTH: 1737
<212> TYPE: DNA
<213> ORGANISM: artificial sequence
<220> FEATURE:
<223> OTHER INFORMATION: YlDLD1 gene

<400> SEQUENCE: 12
atgaacagaa tctcacgagc cgcccagagc gtctctcgaa ttgcctccag gcaattggct      60
cgaagtaact tctccacaca ggcaagatca tcccagccat ctatcagctg gggtgctgtt     120
```

```
gcaggagccg ctggtgtcgc tgcgggagtg acctacttca ttaccaagtc cgacaagaac      180
gctgtggccc ttaagaagga agatgaggat gttggccgag aatccagaa ggtcctcgat       240 ggtgcctctc tcgacacgga cttctctcac aagcccaagt acggaggtga ggaggagttc      300
aagaaggccc tgccggaatt tatcaaggct atcggtgagg aatacgtttc taccgacgag      360
gaggatatcc aattccatgg ctggtccaac gtttcttctt ccaacctcga cactctgccc      420
tttggtgttc tgtaccccaa gtctactgag gaggttctg ccattgccaa gatctgccac       480
aagcacaagc ttcccatggt cggctactcc ggaggtactt ctctggaggg ccacctttct      540
gccgcctacg gagtgtctg catcgacttc tccaacatga acaaaattat tgctattaga       600
cccgatgata tggatgccac tgtccagccc tctgttggct gggttgatct gaacaacgag      660
attctcaagg agggccatcg cctgtttctg gctgttgatc ccggcccaac agcacaggtg      720
ggaggcatgg ttgccaactc ttgttctgga accaactgtg ttaagtacgg acccatgcga      780
gatcacgttg ttaatctcac tgttgtcctg cggacggta ccattctcaa gacccggcag       840
cgacctcgaa agacctctgc tggatacaac ctcaaccatc tattcgctgg aaccgaggga      900
acacttggtc tgatcaccga aatcaccgtt aagctccagc ccatccccaa tgtcacctct      960
gtcgccgtcc aacagtttcc gaccgtccac gccgcttgca agactgctat ggatatcctc     1020
aaggagggta tccccatggc tgctcttgaa cttatggatg atcagcacat gatctgggtc     1080
aacaactccg gttacgccaa gagaaagtgg gaagagaagc ccgccctgtt catgaagttc     1140
gccggtgcct ccgaggaaac tgtcgccgag caggtgaagg ttgctaagga aaggctgcc     1200 aagtacacag actctcccct tgcatttcgga agagatcagg aggaacagga tgagctgtgg    1260
tctgcccgaa aaaacgcgct ttacctcgct cttgctgccg agaaggacgg tatgaaggca    1320
tggaccactg atgttgctgt tcccctttct cagcttcctg atattgtcat gaaggcaaag    1380
cagagcatca ctgatgctgg tcttcttgga ggagttctgg ccacattgg tgacggaaac    1440 taccatgcca tcatgcttta cactcccgag caggccgata ttgtcaccga cgtcgtccat    1500
aagatggtcg accagggtct ggctgccgag ggaacctgca ctggtgagca cggtgttgga    1560
ttcggaaaga tcgaggggct tcttcacgag gttggtcctg tctctctcaa cctgatgcga    1620
accatcaagc tgtctcttga tccccttgag ctacttaacc ccggcaagat cttcactgac    1680
gatgccattc agcagggtct caagactctg ataacaaca aggctggtaa gacttaa       1737
```

```
<210> SEQ ID NO 13
<211> LENGTH: 1149
<212> TYPE: DNA
<213> ORGANISM: artificial sequence
<220> FEATURE:
<223> OTHER INFORMATION: YlCYB21 gene

<400> SEQUENCE: 13
```

```
atgcctatca cccagaagat tctgtcgctc agcgatctgg aggccgcggc catgccctac       60
gccgaaaagg cgcctcgaga ctactgggaa accggatcca acgatctgct gactctggca      120
gagaaccaaa acgccttcaa ctacctcaag atccgggccc gagccatgcg gggcgtcggc      180
accattgaca tctcgcccaa ggtggagctg tttggccgaa agttccgtgc ccccatcggt      240
gtggccccct cagcctacca ccagatggcg gatgattccg gcgagtgtgg cacagctgcg      300
gcttgtcagg cccgaaactg gcccatggga ctttcctctt tctccaacaa gcctctggag      360
gaagtccgag aggctggacc tgatgcagct ctcttcttcc agctctacgt gttcaagaac      420
```

| | |
|---|---|
| aagaagacgt cagagaacct ggtcaagaag gccgaaaagg ccggcttcaa ggccattgcg | 480 |
| ctgaccgtcg acactcccta cctcggaaac cgatacgccg acgtgcgaaa caacttcaag | 540 |
| ctgccatcgc atctctctgc ccgaaacttc gagggcacca ccgaccagcc tattgacaac | 600 |
| gccgccgagg ccgactcgtg ggcccgaaag atcttcaacg gcgaggagtg tcccccgac | 660 |
| gccaacgtgg tcgaccccga tatcaactgg gccgaaacca tcccttggct gcgatccatc | 720 |
| accaacatgc agatctgggt caagggagtc gtgactgccg aggacaccca tgccgccatt | 780 |
| gaggccggcg tggacggaat ctgggtctcc aaccacggtg gccgacagct ggactccggt | 840 |
| ctggccacca ttgacgctct ccccgaggtg gtcgaggccg ctgctggccg agtccccatc | 900 |
| cacattgacg gaggcatccg acgaggagga gacgtgttca aatgccttgc tctgggcgcc | 960 |
| gatttcgtgt ggctgggccg acctgccatc tggggtctca gtacgacgg ccaggccggc | 1020 |
| gtggagctca tggagcagat catcgaggac gatcttaagc tcaccatggc tctggctggc | 1080 |
| accaagaccg tggccgagat caaccgaagc tgtctggttc gaatcggacc cgccatcgtc | 1140 |
| aagctttag | 1149 |

<210> SEQ ID NO 14
<211> LENGTH: 1575
<212> TYPE: DNA
<213> ORGANISM: artificial sequence
<220> FEATURE:
<223> OTHER INFORMATION: gene encoding cytoplasmic CpPCT opt V193A

<400> SEQUENCE: 14

| | |
|---|---|
| atgcgaaagg ttcccatcat cactgctgac gaggctgcca agctcatcaa ggacggagat | 60 |
| accgttacta cttcgggttt tgtcggaaac gctatccctg aggctctgga ccgagctgtc | 120 |
| gagaagcgat tcctcgagac cggcgagcct aagaacatta cttacgttta ctgtggatct | 180 |
| cagggtaacc gagacggacg aggtgctgag cactttgccc atgagggcct gctcaagcga | 240 |
| tacattgctg gacactgggc caccgttccc gctctgggaa agatggccat ggagaacaag | 300 |
| atggaggctt acaacgtgtc ccagggagcc ctgtgccacc tcttccgaga catcgcctcg | 360 |
| cataagcccg tgttttcac caaggtcggc atcggaactt ttattgaccc tcgaaacggc | 420 |
| ggcggcaagg tcaacgacat caccaaggaa gacattgttg agctggtgga gattaagggc | 480 |
| caggagtacc tcttctaccc cgcctttcct atccacgtgg ctctgattcg aggaacctac | 540 |
| gccgacgagt ccggtaacat cacttttgag aaggaagccg ctcccctcga gggaacctct | 600 |
| gtctgtcagg ctgttaagaa ctccggcgga attgtggtcg ttcaggtcga gcgagtggtc | 660 |
| aaggccggaa ctctggaccc ccgacatgtc aaggttcctg gtatctacgt ggattacgtt | 720 |
| gtggtcgctg accccgagga tcaccagcag tcgctggact gcgagtacga tcccgccctc | 780 |
| tctggcgagc atcgacgacc tgaggttgtg ggagagcccc tgcctctctc ggctaagaag | 840 |
| gtcatcggcc gacgaggagc cattgagctg gagaaggacg tggctgtcaa cctcggtgtg | 900 |
| ggagctcctg agtacgtggc ttctgttgct gacgaggaag gcatcgtcga tttcatgacc | 960 |
| ctgactgccg agtctggagc tattggtggc gtgcctgctg aggtgtccg attcggtgcc | 1020 |
| tcctacaacg ccgacgctct gattgatcag ggctaccagt tgactactac gatggcgga | 1080 |
| ggtctggacc tctgttacct gggtctcgct gagtgcgatg agaagggcaa catcaacgtg | 1140 |
| tcccgattcg gtccccgaat tgccggctgt ggcggcttca tcaacattac ccagaacact | 1200 |
| cctaaggttt tcttttgcgg caccttcact gctggtggcc tgaaggtgaa gatcgaggac | 1260 |
| ggcaaggtca tcattgtcca ggaaggcaag cagaagaagt tcctgaaggc cgtcgagcag | 1320 |

-continued

```
atcaccttta acggagacgt tgccctcgct aacaagcagc aggtgaccta cattactgag    1380
cgatgtgtct tcctgctcaa ggaagacggt ctgcacctct ctgagattgc tcctggcatt    1440
gatctgcaga cccagatcct cgacgtgatg gattttgctc ctatcattga ccgagatgcc    1500
aacggccaga ttaagctgat ggatgctgct ctgtttgctg agggtctgat gggcctgaag    1560
gagatgaagt cttaa                                                     1575
```

<210> SEQ ID NO 15
<211> LENGTH: 1680
<212> TYPE: DNA
<213> ORGANISM: artificial sequence
<220> FEATURE:
<223> OTHER INFORMATION: gene encoding PaPhaCp from P. aeruginosa with
      mutations E130D; S325T; S477R; Q481M

<400> SEQUENCE: 15

```
atgtctcaga agaacaacaa cgagctgccc aagcaggccg ccgagaacac cctgaacctg     60
aaccccgtga tcggcatccg aggcaaggac ctgctgacct ctgcccgaat ggtgctgctg    120
caggccgtgc gacagcccct gcactccgcc cgacacgtgg cccacttctc gctcgagctg    180
aagaacgtgc tgctgggcca gtctgagctg cgacccggcg acgacgaccg acgattctct    240
gaccccgcct ggtcccagaa cccctgtac aagcgataca tgcagaccta cctggcctgg    300
cgaaaggagc tgcactcttg gatctctcac tctgacctgt ctccccagga catctctcga    360
ggccagttcg tgatcaacct gctcaccgac gctatgtctc caccaactc cctgtctaac     420 cccgctgccg tgaagcgatt cttcgagact ggcggcaagt ctctgctgga cggcctgggc    480
cacctggcta aggacctggt gaacaacggc ggaatgccct tcaggtgga catggacgcc    540 ttcgaggtgg gcaagaacct ggccaccacc gagggcgccg tggtgttccg aaacgacgtc    600
ctcgagctga tccagtaccg acccatcacc gagtctgtgc acgagcgacc cctgctggtg    660
gtgccccccc agatcaacaa gttctacgtg ttcgacctgt cccccgacaa gtccctggcc    720
cgattctgcc tgcgaaacgg cgtgcagacc ttcatcgtgt cttggcgaaa ccccaccaag    780
tctcagcgag agtggggcct gaccacctac atcgaggccc tgaaggaggc catcgaggtc    840
gtcctgtcta tcaccggctc gaaggacctg aacctcctgg gcgcctgctc tggcggcatc    900
accaccgcca ccctggtggg ccactacgtg gcctctggcg agaagaaggt gaacgccttc    960
acccagctgg tgaccgtgct ggactttgag ctgaacaccc aggtcgccct gttcgccgac   1020
gagaagaccc tcgaggccgc caagcgacga tcttaccagt ctggcgtgct cgagggcaag   1080
gacatggcca aggtgttcgc ctggatgcga cccaacgacc tgatctggaa ctactgggtc   1140
aacaactacc tgctgggcaa ccagcccccct gccttcgaca tcctgtactg gaacaacgac   1200
accacccgac tgcccgctgc cctgcacggc gagttcgtcg agctgttcaa gtccaacccc   1260
ctgaaccgac ccggtgctct cgaggtgtct ggcaccccca tcgacctgaa gcaggtcacc   1320
tgtgacttct actgcgtggc cggcctgaac gaccacatca ccccctggga gtcttgctac   1380
aagtctgccc gactgctggg cggaaagtgc gagttcatcc tgtccaaccg aggccacatc   1440
atgtctatcc tgaaccctcc cggcaacccc aaggctcgat tcatgaccaa ccccgagctg   1500
cctgccgagc ccaaggcctg gctcgagcag gctggcaagc acgccgactc ttggtggctg   1560
cactggcagc agtggctggc cgagcgatct ggcaagaccc gaaaggctcc cgcctctctg   1620
ggcaacaaga cctaccccgc tggcgaggcc gctcccggca cctacgtcca cgagcgataa   1680
```

```
<210> SEQ ID NO 16
<211> LENGTH: 656
<212> TYPE: PRT
<213> ORGANISM: Yarrowia lipolytica

<400> SEQUENCE: 16

Ser Glu Asp His Pro Ala Ile His Pro Pro Ser Glu Phe Lys Asp Asn
1               5                   10                  15

His Pro His Phe Gly Gly Pro His Leu Asp Cys Leu Gln Asp Tyr His
            20                  25                  30

Gln Leu His Lys Glu Ser Ile Glu Asp Pro Lys Ala Phe Trp Lys Lys
        35                  40                  45

Met Ala Asn Glu Leu Ile Ser Trp Ser Thr Pro Phe Glu Thr Val Arg
    50                  55                  60

Ser Gly Gly Phe Glu His Gly Asp Val Ala Trp Phe Pro Glu Gly Gln
65                  70                  75                  80

Leu Asn Ala Ser Tyr Asn Cys Val Asp Arg His Ala Phe Ala Asn Pro
                85                  90                  95

Asp Lys Pro Ala Ile Ile Phe Glu Ala Asp Glu Pro Gly Gln Gly Arg
            100                 105                 110

Ile Val Thr Tyr Gly Glu Leu Leu Arg Gln Val Ser Gln Val Ala Ala
        115                 120                 125

Thr Leu Arg Ser Phe Gly Val Gln Lys Gly Asp Thr Val Ala Val Tyr
    130                 135                 140

Leu Pro Met Ile Pro Glu Ala Ile Val Thr Leu Leu Ala Ile Thr Arg
145                 150                 155                 160

Ile Gly Ala Val His Ser Val Ile Phe Ala Gly Phe Ser Ser Gly Ser
                165                 170                 175

Leu Arg Asp Arg Ile Asn Asp Ala Lys Ser Lys Val Val Val Thr Thr
            180                 185                 190

Asp Ala Ser Met Arg Gly Gly Lys Thr Ile Asp Thr Lys Lys Ile Val
        195                 200                 205

Asp Glu Ala Leu Arg Asp Cys Pro Ser Val Thr His Thr Leu Val Phe
    210                 215                 220

Arg Arg Ala Gly Val Glu Asn Leu Ala Trp Thr Glu Gly Arg Asp Phe
225                 230                 235                 240

Trp Trp His Glu Glu Val Val Lys His Arg Pro Tyr Leu Ala Pro Val
                245                 250                 255

Pro Val Ala Ser Glu Asp Pro Ile Phe Leu Leu Tyr Thr Ser Gly Ser
            260                 265                 270

Thr Gly Thr Pro Lys Gly Leu Ala His Ala Thr Gly Gly Tyr Leu Leu
        275                 280                 285

Gly Ala Ala Leu Thr Ala Lys Tyr Val Phe Asp Ile His Gly Asp Asp
    290                 295                 300

Lys Leu Phe Thr Ala Gly Asp Val Gly Trp Ile Thr Gly His Thr Tyr
305                 310                 315                 320

Val Leu Tyr Gly Pro Leu Met Leu Gly Ala Thr Thr Val Val Phe Glu
                325                 330                 335

Gly Thr Pro Ala Tyr Pro Ser Phe Ser Arg Tyr Trp Asp Ile Val Asp
            340                 345                 350

Asp His Lys Ile Thr His Phe Tyr Val Ala Pro Thr Ala Leu Arg Leu
        355                 360                 365

Leu Lys Arg Ala Gly Thr His Ile Lys His Asp Leu Ser Ser Leu
    370                 375                 380
```

Arg Thr Leu Gly Ser Val Gly Glu Pro Ile Ala Pro Asp Val Trp Gln
385                 390                 395                 400

Trp Tyr Asn Asp Asn Ile Gly Arg Gly Lys Ala His Ile Cys Asp Thr
            405                 410                 415

Tyr Trp Gln Thr Glu Thr Gly Ser His Ile Ile Ala Pro Met Ala Gly
            420                 425                 430

Val Thr Pro Thr Lys Pro Gly Ser Ala Ser Leu Pro Val Phe Gly Ile
            435                 440                 445

Asp Pro Val Ile Ile Asp Pro Val Ser Gly Glu Leu Lys Gly Asn
            450                 455                 460

Asn Val Glu Gly Val Leu Ala Leu Arg Ser Pro Trp Pro Ser Met Ala
465                 470                 475                 480

Arg Thr Val Trp Asn Thr His Glu Arg Tyr Met Glu Thr Tyr Leu Arg
            485                 490                 495

Pro Tyr Pro Gly Tyr Tyr Phe Thr Gly Asp Gly Ala Ala Arg Asp Asn
            500                 505                 510

Asp Gly Phe Tyr Trp Ile Arg Gly Arg Val Asp Val Val Asn Val
            515                 520                 525

Ser Gly His Arg Leu Ser Thr Ala Glu Ile Glu Ala Ala Leu Ile Glu
530                 535                 540

His Ala Gln Val Ser Glu Ser Ala Val Val Gly Val His Asp Asp Leu
545                 550                 555                 560

Thr Gly Gln Ala Val Asn Ala Phe Val Ala Leu Lys Asn Pro Val Glu
            565                 570                 575

Asp Val Asp Ala Leu Arg Lys Glu Leu Val Val Gln Val Arg Lys Thr
            580                 585                 590

Ile Gly Pro Phe Ala Ala Pro Lys Asn Val Ile Val Asp Asp Leu
            595                 600                 605

Pro Lys Thr Arg Ser Gly Lys Ile Met Arg Arg Ile Leu Arg Lys Val
            610                 615                 620

Leu Ala Gly Glu Glu Asp Gln Leu Gly Asp Ile Ser Thr Leu Ala Asn
625                 630                 635                 640

Pro Asp Val Val Gln Thr Ile Ile Glu Val Val His Ser Leu Lys Lys
            645                 650                 655

<210> SEQ ID NO 17
<211> LENGTH: 139
<212> TYPE: PRT
<213> ORGANISM: Pseudomonas putida

<400> SEQUENCE: 17

Met Ala Lys Val Thr Val Lys Lys Asp Asp Ala Leu Gly Thr Leu
1               5                   10                  15

Gly Glu Val Arg Gly Tyr Ala Arg Lys Ile Trp Leu Ala Gly Ile Gly
            20                  25                  30

Ala Tyr Ala Arg Val Gly Gln Glu Gly Ser Asp Tyr Phe Gln Glu Leu
        35                  40                  45

Val Lys Ala Gly Glu Gly Val Glu Lys Arg Gly Lys Lys Arg Ile Asp
    50                  55                  60

Lys Glu Leu Asp Ala Ala Asn Asn Gln Ile Asp Glu Ala Ala Glu Glu
65                  70                  75                  80

Val Ser Arg Val Arg Gly Glu Val Glu Ile Gln Leu Asp Lys Ile Glu
            85                  90                  95

Lys Ala Phe Asp Ala Arg Val Gly Arg Ala Leu Asn Arg Leu Gly Ile
            100                 105                 110

```
Pro Ser Lys His Asp Val Glu Ala Leu Ser Ile Lys Leu Glu Gln Leu
            115                 120                 125

His Glu Leu Leu Glu Arg Val Ala His Lys Pro
        130                 135

<210> SEQ ID NO 18
<211> LENGTH: 192
<212> TYPE: PRT
<213> ORGANISM: artificial sequence
<220> FEATURE:
<223> OTHER INFORMATION: phaP1p from Rastonia eutropha H16 (Q0KBV4)

<400> SEQUENCE: 18

Met Ile Leu Thr Pro Glu Gln Val Ala Ala Gln Lys Ala Asn Leu
1               5                   10                  15

Glu Thr Leu Phe Gly Leu Thr Thr Lys Ala Phe Glu Gly Val Glu Lys
                20                  25                  30

Leu Val Glu Leu Asn Leu Gln Val Val Lys Thr Ser Phe Ala Glu Gly
                35                  40                  45

Val Asp Asn Ala Lys Lys Ala Leu Ser Ala Lys Asp Ala Gln Glu Leu
    50                  55                  60

Leu Ala Ile Gln Ala Ala Val Gln Pro Val Ala Glu Lys Thr Leu
65                  70                  75                  80

Ala Tyr Thr Arg His Leu Tyr Glu Ile Ala Ser Glu Thr Gln Ser Glu
                85                  90                  95

Phe Thr Lys Val Ala Glu Ala Gln Leu Ala Glu Gly Ser Lys Asn Val
                100                 105                 110

Gln Ala Leu Val Glu Asn Leu Ala Lys Asn Ala Pro Ala Gly Ser Glu
            115                 120                 125

Ser Thr Val Ala Ile Val Lys Ser Ala Ile Ser Ala Ala Asn Asn Ala
        130                 135                 140

Tyr Glu Ser Val Gln Lys Ala Thr Lys Gln Ala Val Glu Ile Ala Glu
145                 150                 155                 160

Thr Asn Phe Gln Ala Ala Ala Thr Ala Ala Thr Lys Ala Ala Gln Gln
                165                 170                 175

Ala Ser Ala Thr Ala Arg Thr Ala Thr Ala Lys Lys Thr Thr Ala Ala
            180                 185                 190
```